United States Patent [19]

McGuire et al.

[11] Patent Number: 5,422,428

[45] Date of Patent: Jun. 6, 1995

[54] IMMUNIZATION AGAINST BABESIOSIS USING PURIFIED SURFACE ANTIGENS OF BABESIA BIGEMINA AND SIMILAR IMMUNOGENS

[75] Inventors: Travis C. McGuire; Terry F. McElwain; Lance E. Perryman; William C. Davis, all of Pullman, Wash.

[73] Assignee: Washington State University, Pullman, Wash.

[21] Appl. No.: 803,636

[22] Filed: Dec. 6, 1991

Related U.S. Application Data

[63] Continuation-in-part of Ser. No. 663,255, Mar. 1, 1991, Pat. No. 5,209,929, which is a continuation of Ser. No. 31,328, Mar. 27, 1987, abandoned.

[51] Int. Cl.⁶ ............................................ C07K 14/44
[52] U.S. Cl. .................................. 530/350; 530/395; 530/855; 424/266.1; 424/270.1

[56] References Cited

U.S. PATENT DOCUMENTS

| 4,661,348 | 4/1987 | Wright | 424/88 |
|---|---|---|---|
| 4,762,711 | 8/1988 | Buening et al. | |
| 5,209,929 | 5/1993 | McGuire et al. | 424/88 |

OTHER PUBLICATIONS

Wright, I. G. et al. Infect. Immun. 55(2) 364–8. Feb. 1987. "Protection of *Babesis bigemins*-immune animals against subsequent challenge with virulent *B. bovis*".
Cowman, A. F., P. Timms, D. J. Kemp (1984) "DNA Polymorphisms and Subpopulations in *Babesia bovis*," Mol. Biochem. Parasitol. 11:91–103.
Gill, A. C., A. F. Cowman, N. P. Stewart, D. J. Kemp. P. Timms (1987) "[Babesia bovis: Molecular and Biological Characteristics of Cloned Parasite Lines," Exp. Parasitol. 63:180–188.
Hall, W. T. K., L. Tammemagi, L. A. Y. Johnson (1968) "Bovine babesiosis: The immunity of calves to *Babesia bigemina* infection," Aust. Vet. J. 44:259–264.
Mahoney, D. F., I. G. Wright, G. B. Mirre (1973) "Bovine babesiasis: The persistence of immunity to *Babesia argentina* and *B. bigemina* in calves (Bos taurus) after naturally acquired infection," Ann. Trop. Med. Parasitol. 67(2):197–203.
Callow, L. L. (1977) "Vaccination Against Bovine Babesiosis," *In Immunity to Blood Parasites of Animals and Man*, Plenum Press, N.Y., pp. 121–149.
Dagliesh, R. J., L. L. Callow, L. T. Mellors, W. McGregor (1981) "Development of a highly infective *Babesia bigemina* vaccine of reduced virulence," Austr. Vet. J. 57:8–11.
Smith, R. D., M. A. James, M. Ristic (1981) "Bovine Babesiosis: Protection of Cattle with Culture–Derived Soluble *Babesia bovis* Antigen," Science 212:335–338.
Wright, I. G., G. B. Mirre, K. Rose-Bramanis, M. Chamberlain, B. V. Goodger, D. J. Waltisbuhl (1985) "Protective Vaccination Against Virulent *Babesia bovis* with a Low–Molecular–Weight Antigen," Infect. Immun. 48(1):109–113.
Commins, M. A., B. V. Goodger, I. G. Wright (1985) "Proteinases in the lysate of bovine erythrocytes infected with *Babesia bovis*: Initial vaccination studies," Int. J. Parasitol. 15(5):491–495.
Waltisbuhl, D. J., B. V. Goodger, I. G. Wright, G. B. Mirre, M. A. Commins (1987) "*Babesia bovis*: Vaccina- (List continue on next page.)

Primary Examiner—Christine M. Nucker
Assistant Examiner—Thomas Cunningham
Attorney, Agent, or Firm—Saliwanchik & Saliwanchik

[57] ABSTRACT

Antigenic surface proteins from the intraerythrocytic merozoite stage of *Babesia bigemina* have been isolated using cell fusions and monoclonal antibodies produced thereby. The gene encoding a 58 kD surface protein has been identified and the DNA sequence determined and compared with sequences of other known merozoite proteins. Immunization of mammals, such as bovines, with purified isolates induces an immunological response that is effective to reduce pathological effects of babesiosis induced by *Babesia bigemina*. Diagnostic kits using monoclonal antibodies and antigenic surface proteins of *Babesia bigemina* are also disclosed.

4 Claims, 9 Drawing Sheets

OTHER PUBLICATIONS tion studies with three groups of high molecular weight antigens from lysate of infected erythrocytes," Parasitol. Res. 73:319–323.

Montenegro-James, S., M. Toro Benitez, E. Leon, R. Lopez, M. Ristic (1987) "*Bovine babesiosis:* induction of protective immunity with culture–derived *Babesia bovis* and *Babesia bigemina* immunogens," Parasitol. Res. 74:142–150.

Goodger, B. V., M. A. Commins, I. G. Wright, D. J. Waltisbuhl, G. B. Mirre (1987) "Successful homologous vaccination against *Babesia bovis* using a heparin-binding fraction of infected erythrocytes," Int. J. Parasito. 17(4):935–940.

Goodger, B. V., I. G. Wright, D. J. Waltisbuhl, G. B. Mirre (1985) "*Babesia bovis:* successful vaccination against homologous challenge in spenectomised calves using a fraction of haemagglutinating antigen," Int. J. Parasitol. 15(2):175–179.

Goff, W. L., W. C. Davis, G. H. Palmer, T. F. McElwain, W. C. Johnson, J. F. Bailey, T. C. McGuire (1988) "Identification of *Babesia bovis* Merozoite Surface Antigens by Using Immune Bovine Sera and Monoclonal Antibodies," Infect. Immun. 56(9):2363–2368.

McElwain, T. F., L. E. Perryman, W. C. Davis, T. C. McGuire (1987) "Antibodies Define Multiple Proteins with Epitopes Exposed on the Surface of Live *Babesia bigemina* Merozoites," J. Immunol. 138(7):2298–2304.

Callow, L. L., W. McGregor, R. J. Parker, R. J. Dalglisch (1974) "Immunity of cattle to *Babesia bigemina* following its elimination from the host, with observations on antibody levels detected by the indirect fluorescent antibody test," Austral. Vet. J. 50:12–15.

Kuttler, K. L., L. W. Johnson (1979) "Immunization of Cattle with a *Babesia bigemina* Antigen in Freund's Complete Adjuvant," Am. J. Vet. Res. 41(4):536–538.

Figueroa, J. V., G. M. Buening, D. A. Kinden, T. J. Greem (1990) "Identification of common surface antigens among *Babesia bigemina* isolates by using monoclonal antibodies," Parasitol. 100:161–175.

Figueroa, J. V., G. M. Buening (1991) "In Vitro Inhibition of Multiplication of *Babesia bigemina* by Using Monoclonal Antibodies," J. Clin. Microbiol. 29(5):997–1003.

Callow, L. L., L. T. Mellors, W. McGregor (1979) "Reduction in Virulence of *Babesia bovis* Due to Rapid Passage in Splenectomized Cattle," Int. J. Parasitol. 9:333–338.

Kuttler, K. L., M. G. Levy, M. A. James, M. Ristic (1981) "Efficacy of nonviable culture-derived *Babesia bovis* vaccine," Am. J. Vet. Res. 43(2):281–284.

Kuttler, K. L., M. G. Levy, M. Ristic (1983) "Cell culture-derived *Babesia bovis* vaccine: Sequential challenge exposure of protective immunity during a 6–month postvaccination period," Am. J. Vet. Res. 44(8):1456–1459.

Timms, P., R. J. Dalgliesh, D. N. Barry, C. K. Dimmock, B. J. Rodwell (1983) "*Babesia bovis:* comparison of culture–derived parasites, non-living antigen and conventional vaccine in the protection of cattle against heterologous challenge," Austral. Vet. J. 60:75–77.

Wright, I. G., M. White, P. D. Tracey-Patte, K. A. Donaldson, B. V. Goodger, D. J. Waltisbuhl, D. F. Mahoney (1983) "*Babesia bovis: Isolation of a Protective Antigen by Using Monoclonal Antibodies,*" *Infect. Immun.* 41:244–250.

```
p58    ..FLGVCFGALLLV.ARSGSAIRYTHRSGVM.SAEVVGDVSKTLLEANEV            46
       :::..:.|.|:.|||::.:.|:|||.|||||.||:|||||||||||||||
Bv60   MRIISGVVGCLFLVFSHHVSAFRHNQRVGSLAPAEVVGDLTSTLETADTL            50 p58    VNAEMEATQVNKDMQSQLSNVKETIVGEVCEKVAGNSTCGESVIAYVNRC            96
       :.:..:.|:|:|:|||:::|||.::.|||::|.|:|||.:||:|:||||
Bv60   MTLRDHMHNITKDMKHVLSNGREQIVNDVCSNAPEDSNCREVVNNYADRC           100 p58    DEGDCLTLDSMK......YKPLSLPNPYQLDAAFMLFRESDSNPAKNEVK           140
       :.|:|:|:|:|.......||||||||||||||||||:|||||||||:||
Bv60   EMYGCFTIDNVKYPLYQEYQPLSLPNPYQLDAAFRLFKESASNPAKNSVK           150 p58    RFWMRSRSS...HGDYHHFVVSLLKKNVVRDPESNDVENFASQYFYMTTLY           188
       |.:||||:..:|.|:||:|||||.||||..|:||:||:|||||.|||||
Bv60   REWLRFRNGANHGDYHYFVTGLLNNNVHEEGTTDVEYLVNKVLYMATMN            200 p58    YKTYLTVDFTAAKFFNKLAFTTRLFGFGIQKALKRLVRSNLPVDLGTHPE           238
       ||||||||.||.|||||:|.:.:||||:|:|:|||||||||||||:|||
Bv60   YKTYLTVNSMNAKFFNRFSFTTKIFSRRIRQTLSDIIRWNVPEDFEERSI           250 p58    ATIREIASGYGEYMTQVPAMTSFAERFSKMATKTLLVTVSDYVHLPAYK            288
       :|:::|:||||:|.:|:|::|:|||:||:.|::.||.:|||:|::.||:
Bv60   ERITQLTSSYEDYMLTQIPTLSKFARRYADMVKKVLLGSLTSYVEAPWYK           300 p58    RWYRKFKEFIVNFFTDPAK
       |.:|||:||:..|::|||:
Bv60   RWIKKFRDFFSKNVTQPTK
```

Figure 1

```
 7  tatggcacattggcgcataagcactcccaataagtgattgtgaacgcggaattaggtcggccgtgccgtttttccgttagaataatatttcaagcagatt  100
 9  tatggcacattggcgcataagcactcccaataagtgattgtgaacgcggaattaggtcggccgtgccgtttttccgttagaataatatttcaagcagatt  100
14  tatggcacattggcgcataagcactcccaataagtgattgtgaacgcggaattaggtcggccgtgccgtttttccgttagaataatatttcaagcagatt  100
13  tatggcacattggcgcataagcactcccaataagtgattgtgaacgcggaattaggtcggccgtgccgtttttccgttagaataatatttcaagcagatt  100
    ....................................................................................................

7  cgtctaatcgttctgctgtcactatcgtaatacacatagcgttgtctgctaacgttttgtgagcaacattcccattgcgtaacaATGAGGAGCTTCTTG  200
 9  cgtctaatcgttctgctgtcactatcgtaatacacatagcgttgtctgctaacgttttgtgagcaacattcccattgcgtaacaATGAGGAGCTTCTTG  200
14  cgtctaatcgttctgctgtcactatcgtaatacacatagcgttgtctgctaacgttttgtgagcaacattcccattgcgtaacaATGAGGAGCTTCTTG  200
13  cgtctaatcgttctgctgtcactatcgtaatacacatagcgttgtctgctaacgttttgtgagcaacattcccattgcgtaacaATGAGGAGCTTCTTG  200
    ....................................................................................................

7  GGTGTGTTTGGAGCTCTCTTGCTCTCGTAGCAAGGAGCGGTTCTCTATTCGCTATACTCACCGTTCGGGTGTTATGTCAGCAGAGGTGGTTGGAGATG  300
 9  GGTGTGTTTGGAGCTCTCTTGCTCTCGTAGCAAGGAGCGGTTCTCTATTCGCTATACTCACCGTTCGGGTGTTATGTCAGCAGAGGTGGTTGGAGATG  300
14  GGTGTGTTTGGAGCTCTCTTGCTCTCGTAGCAAGGAGCGGTTCTCTATTCGCTATACTCACCGTTCGGGTGTTATGTCAGCAGAGGTGGTTGGAGATG  300
13  GGTGTGTTTGGAGCTCTCTTGCTCTCGTAGCAAGGAGCGGTTCTCTATTCGCTATACTCACCGTTCGGGTGTTATGTCAGCAGAGGTGGTTGGAGATG  300
    ....................................................................................................

7  TGTCCAAGACCTTGCTGGAAGCCAATGAGGTTGTCAATGCTGAAATGGAAGCAACTCAGGTCAACAAAGATATGCAAAGTCAATTGTCTAATGTTAAGGA  400
 9  TGTCCAAGACCTTGCTGGAAGCCAATGAGGTTGTCAATGCTGAAATGGAAGCAGCTCAGATTAACGAAGATTCAGTTGGCAACGTCAAGA         400
14  TGTCCAAGACCTTGCTGGAAGCCAATGAGGTTGTCAATGCTGAAATGGAAGCAGCTCAGATTAACGAAGATTCAGTTGGCAACGTCAAGA         400
13  TGTCCAAGACCTTGCTGGAAGCCAATGAGGTTGTCAATGCTGAAATGGAAGCAACTCAGGTCAACAAAGATATGCAAAGTCAATTGTCTAATGTTAAGGA  400
    ....+........+........+........+........+...*

7  GACCATTGTTGGTGAGGTCTGCGAGAAGTTGCTGGAAACTCTACCTGCGGTGAGAGCGTAATTGCCTATGTTAACCGTTGTGATGAGGCGATTGTCTG  500
 9  GACCATCGTTGATGAGGTCTGCGAGAAGTTGCTGGAAACTCTACCTGCGGTGAGAGCGTAATTGCCTATGTTAACCGTTGTGATGAGGGCGATTGTCTG  500
14  GACCATCGTTGATGAGGTCTGCGAGAAGTTGCTGGAAACTCTACCTGCGGTGAGAGCGTAATTGCCTATGTTAACCGTTGTGATGAGGGCGATTGTCTG  500
13  GACCATTGTTGGTGAGGTCTGCGAGAAGTTGCTGGAAACTCTACCTGCGGTGAGAGCGTAATTGCCTATGTTAACCGTTGTGATGAGGCGATTGTCTG  500
    ....+....*
```

Figure 2A

```
 7  ACGCTTGACAGCATGAAGTACAAGCCGTTGAGTCTGCCAAATCCTTACCAGTTGGACGCTGCCTTCATGCTTTTCAGGGAAAGTGATTCTAACCCTGCGA  600
 9  ACGCTTGACAGCATGAAGTACAAGCCGTTGAGTCTGCCAAATCCTTACCAGTTGGACGCTGCCTTCATGCTTTTCAGGGAAAGTGATTCTAACCCTGCGA  600
14  ACGCTTGACAGCATGAAGTACAAGCCGTTGAGTCTGCCAAATCCTTACCAGTTGGACGCTGCCTTCATGCTTTTCAGGGAAAGTGATTCTAACCCTGCGA  600
13  ACGCTTGACAGCATGAAGTACAAGCCGTTGAGTCTGCCAAATCCTTACCAGTTGGACGCTGCCTTCATGCTTTTCAGGGAAAGTGATTCTAACCCTGCGA  600
    ....................................................................................................

7  AGAATGAGGTGAAGCGCTTCTGGATGCGTTCGAGGAGCAGCCACGGCGACTACCATCACTTTGTTGTTAGCTTGTTGTTGAAGAAGAATGTTGTACGGACCC  700
 9  AGAATGAGGTGAAGCGCTTCTGGATGCGTTCGAGGAGCAGCCACGGCGACTACCATCACTTTGTTGTTAGCTTGTTGTTGAAGAAGAATGTTGTACGGACCC  700
14  AGAATGAGGTGAAGCGCTTCTGGATGCGTTCGAGGAGCAGCCACGGCGACTACCATCACTTTGTTGTTAGCTTGTTGTTGAAGAAGAATGTTGTACGGACCC  700
13  AGAATGAGGTGAAGCGCTTCTGGATGCGTTCGAGGAGCAGCCACGGCGACTACCATCACTTTGTTGTTAGCTTGTTGTTGAAGAAGAATGTTGTACGGACCC  700
    ..............................................+.....................................................

7  TGAATCCAATGATGATGTTGAGAACTTCGCATCGCAGTACTTCTACATGACTACGTTGACTTACGGGCGGCTAAGTTC  800
 9  TGAATCCAATGATGATGTTGAGAACTTCGCATCGCAGTACTTCTACATGACTACGTTGACTTACGGGCGGCTAAGTTC  800
14  TGAATCCAATGATGATGTTGAGAACTTCGCATCGCAGTACTTCTACATGACTACGTTGACTTACGGGCGGCTAAGTTC  800
13  TGAATCCAATGATGATGTTGAGAACTTCGCATCGCAGTACTTCTACATGACTACGTTGACTTACGGGCGGCTAAGTTC  800
    ....................................................................................................

7  TTCAACAAGCTTGCTTTCACAACTCGCCTTCGGTTTCGGTTTCGGTATCCAGAAGCGTTGAAGCGTTGGTAGGAGCAACCTTCCCGTTGACCTTGGAACCC  900
 9  TTCAACAAGCTTGCTTTCACAACTCGCCTTCGGTTTCGGTTTCGGTATCCAGAAGCGTTGAAGCGTTGGTAGGAGCAACCTTCCCGTTGACCTTAGAACCC  900
14  TTCAACAAGCTTGCTTTCACAACTCGCCTTCGGTTTCGGTTTCGGTATCCAGAAGCGTTGAAGCGTTGGTAGGAGCAACCTTCCCGTTGACCTTGGAACCC  900
13  TTCAACAAGCTTGCTTTCACAACTCGCCTTCGGTTTCGGTTTCGGTATCCAGAAGCGTTGAAGCGTTGGTAGGAGCAACCTTCCCGTTGACCTTGGAACCC  900
    ...........................................................................................*........

7  ACCCTGAGGCCACCATCCGGCCACATCCGGCGAAATAGCTAGGGCTACGGGCGAGTACATGATGACCCAGGTGCCTGCCTGCGATGACCTCGTTGAGCGTTTCTCCAAGAT  1000
 9  ACCCTGAGGCCACCATCCGGCCACATCCGGCGAAATAGCTAGGGCTACGGGCGAGTACATGATGACCCAGGTGCCTGCCTGCGATGACCTCGTTGAGCGTTTCTCCAAGAT  1000
14  ACCCTGAGGCCACCATCCGGCCACATCCGGCGAAATAGCTAGGGCTACGGGCGAGTACATGATGACCCAGGTGCCTGCCTGCGATGACCTCGTTGAGCGTTTCTCCAAGAT  1000
13  ACCCTGAGGCCACCATCCGGCCACATCCGGCGAAATAGCTAGGGCTACGGGCGAGTACATGATGACCCAGGTGCCTGCCTGCGATGACCTCGTTGAGCGTTTCTCCAAGAT  1000
    ...........................................................................................*..++....
```

```
 7  AGGGATTCCGAAGAGAAGAAATTCTCAAGGAATCACAATATAATTCAGATCGCGAAAATGATGAGGACTCATCCGACGAGTCAGCAGCATATGAAACTGCTCCGG  1500
 9  AGGGATTCCGAAGAGAAGAAATTCTCAAGGAATCACAATATAATTCAGATCGCGAAAATGATGAGGACTCATCCGACGAGTCAGCAGCATATGAAACTGCTCCGG  1500
14  A-----TCCGAAG------------CAG-----CTGTAGAGGAAACCGTTC-CGTCT------GGCGATTCCGCGGAAACTGAATTTGAGG--TC-CCTG      1455
13  A-----TCCGAAG------------CAG-----CTGTAGAGGAAACCGTTC-CGTCT------GGCGATTCCGCGGAAACTGAATTTGAGG--TC-CCTG      1455
    .........        .*         .*+*...+*.**...++..**...+.*.......**..+.*

7  AATCCACTAGACTAAtcggctaaaaaggccatgcatgatcgcattgtatgcaattgaatgttaagcaaaagtattacaacagtttacataactctaccg       1600
 9  AATCACTAGACTAAtcggctaaaaaggccatgcatgatcgcattgtatgcaattgaatgttaagcaaaagtattacaacagtttacataactctaccg        1600
14  AAGAACAATACGTCGATGCTGTTA-----CTACTCAGGAG---GTTAACAGCGAGAAGGT-TGATGCCGACGATG---CGGGTAATGCCGAAACCCAGCAG      1544
13  AAGAACAATACGTCGATGCTGTTA-----CTACTCAGGAG---GTTAACAGCGAGAAGGT-TGATGCCGACGATG---CGGGTAATGCCGAAACCCAGCAG      1544
    ..*..*.**+*+*...***.....+.*..*........+.**.*..*****..*..+.**..+.**..+.+.

7  atataatgaacaataagactaatgctgacaaataatac----gttgatacaacaacatttgtacgtaaat---agttacg--actgcatcata-caaaa      1688
 9  atataatgaacaataagactaatgctgacaaataatac----gttgatacaacaacatttgtacgtaaat---agttacg--actgcatcata-caaaa      1688
14  CTTCCAGATGCAGAAATGAAGTGCGCGCTGATGACCCCAAAATGAGGATTCTTCAAGTTCTTCAGATGATTCAGATGATTCAGAtcagcaattagctgta    1644
13  CTTCCAGATGCAGAAATGAAGTGCGCGCTGATGACCCCAAAATGAGGATTCTTCAAGTTCTTCAGATGATTCAGATGATTCAGAtcagcaattagctgta    1644
    +.*++.****..**..*+**.*...**++*..+.*+..***..*........***

7  ---ttcaacgctgctactgtgaatcgccatataacaatttcgaatgcctaatctccatcgttttttacttttatgttggtcaggtgttcatatttg         1787
 9  ---ttcaacgctgctactgtgaatcgccatataacaatttcgaatgcctaatctccatcgttttttacttttatgttggtcaggtgttcatatttg         1787
14  catttcgatagtgttgctgttgtcaaataatcgccatataacaatttcgaatgcctaatctccatcgttttttacttttatgttggtcaggtgttcatatttg  1744
13  catttcgatagtgttgctgttgtcaaataatcgccatataacaatttcgaatgcctaatctccatcgttttttacttttatgttggtcaggtgttcatatttg  1744
    .......+.*........+.
```

Figure 2D

```
 7  ccaaggcaccgtgctgctgagatcgctgcgtcattttttgcgtgtgtaatatgtcgtataatatgctcccatgctgcgctgctattcgctacatgcgctgccaa  1887
 9  ccaaggcaccgtgctgctgagatcgctgcgtcattttttgcgtgtgtaatatgtcgtataatatgctcccatgctgcgctgctattcgctacatgcgctgccaa  1887
14  ccaaggcaccgtgctgctgagatcgctgcgtcattttttgcgtgtgtaatatgtcgtataatatgctcccatgctgcgctgctattcgctacatgcgctgccaa  1844
13  ccaaggcaccgtgctgctgagatcgctgcgtcattttttgcgtgtgtaatatgtcgtataatatgctcccatgctgcgctgctattcgctacatgcgctgccaa  1844
         .....                                                                                   .....

7  catggccgtagatagcgtgtctgcaggcaacgctgcaataataaaaaatgtcgtgactgagttacgcacgcgccataacgttatacaatcagtattagaa  1987
 9  catggccgtagatagcgtgtctgcaggcaacgctgcaataataaaaaatgtcgtgactgagttacgcacgcgccataacgttatacaatcagtattagaa  1987
14  catggccgtagatagcgtgtctgcaggcaacgctgcaataataaaaaagtgtcgtgactgagttacgcacgcgccataacgttatacaatcagtattagaa  1944
13  catggccgtagatagcgtgtctgcaggcaacgctgcaataataaaaaagtgtcgtgactgagttacgcacgcgccataacgttatacaatcagtattagaa  1944
                                                  *
 7  gagtacagcgtcgactgc  2005
 9  gagtacagcgtcgactgc  2005
14  gagtacagcgtcgactgc  1962
13  gagtacagcgtcgactgc  1962
         .....
```

Figure 2E

```
p58v 7   MRSFLGVCFGALLLVARSGSAIRYTHRSGVMSAEVVGDVSKTLLEANEVVNAEMEATQVNKDMQSLSNVKETIV   75
p58v 9   MRSFLGVCFGALLLVARSGSAIRYTHRSGVMSAEVVGDVSKTLLAANEVVNAEHEAAQINEDMKIQLANVKETIV  75
p58v14   MRSFLGVCFGALLLVARSGSAIRYTHRSGVMSAEVVGDVSKTLLAANEVVNAEMEAAQINEDMKIQLANVKETIV  75
p58v13   MRSFLGVCFGALLLVARSGSAIRYTHRSGVMSAEVVGDVSKTLLEANEVVNAEMEATQVNKDMQSLSNVKETIV   75
         ..........................................*.*.*..*.*..* p58v 7   GEVCEKVAGNSTCGESVIAYVNRCDEGDCLTLDSMKYKPLSLPNPYQLDAAFMLFRESDSNPAKNEVKRFWMRSR  150
p58v 9   DEVCRKDAGSPTCRKSVIAYVDRCDEGDCLTLDSMKYKPLSLPNPYQLDAAFMLFRESDSNPAKNEVKCFWMRSR  150
p58v14   DEVCRKDAGSPTCRKSVIAYVDRCDEGDCLTLDSMKYKPLSLPNPYQLDAAFMLFRESDSNPAKNEVKRFWMRSR  150
p58v13   GEVCEKVAGNSTCGESVIAYVNRCDEGDCLTLDSMKYKPLSLPNPYQLDAAFMLFRESDSNPAKNEVKRFWMRSR  150
         *...+.+..**..+*..........................................* p58v 7   SSHGDYHHFVVSLLKKNVVRDPESNDVENFASQYFYMTTLYYKTYLTVDFTAAKFFNKLAFTTRLFGFGIQKALK  225
p58v 9   SSHGDYHHFVVSLLKKNVVRDPESNDVENFASQYFYMTTLYYKTYLTVDFTAAKFFNKLAFTTRLFGFGIQKALK  225
p58v14   SSHGDYHHFVVSLLKKNVVRDPESNDVENFASQYFYMTTLYYKTYLTVDFTAAKFFNKLAFTTRLFGFGIQKALK  225
p58v13   SSHGDYHHFVVSLLKKNVVRDPESNDVENFASQYFYMTTLYYKTYLTVDFTAAKFFNKLAFTTRLFGFGIQKALK  225
         ..........................................* p58v 7   RLVRSNLPVDLGTHPEATIREIASGYGEYMMTQVPAMTSFAERFSKMATKTLLVTVSDYVHLPAYKRWYRKFKEF  300
p58v 9   RLVRSNLPVDLRTHPEATIREIASGYGEYMMTQVPAMTSFAEAFSKMATKTLLVTVSDYVHLPAYKRWYRKFKEF  300
p58v14   RLVRSNLPVDLGTHPEATIREIASGYGEYMMTQVPAMTSFAGRFSKMATKTLLVTVSDYVHLPAYKRWYRKFKEF  300
p58v13   RLVRSNLPVDLGTHPEATIREIASGYGEYMMTQVPAMTSFAERFSKMATKTLLVTVSDYVHLPAYKRWYRKFKEF  300
         ...........*..............................*+.
```

Figure 4A

```
p58v 7   IVNFFTDPAKLIMKHVSQPVKTAYTKLVPEEHRQAIRNVVGQSTKHIANGVRDLARMIKEPSQQIIREKLPHYLS  375
p58v 9   IVNFFTDPAKLIMKHVSQPVKTAYTKLVPEEHRQAIRNVVGQSTKHIANGVRDLARMIKEPSQQIIREKLPHYLS  375
p58v14   IVNFFTDPAKLIMKHVSQPVKTAYTKLVPEEHRQAIRNVVGQSTKHIANGVRDLSRMIKEPSQQIIREKLPHYLS  375
p58v13   IVNFFTDPAKLIMKHVSQPVKTAYTKLVPEEHRQAIRNVVGQSTKHIANGVRDLSRMIKEPSQQIIREKLPHYLS  375
         ································································*········· p58v 7   KAKGAVEHVVDKVVKSKT-FKKRA-----------GESSEESYRDSEEEILK---------------E        415
p58v 9   KAKGAVEHVVDKVVKSKT-FKKRA-----------GESSEESYRDSEEEILK---------------E        415
p58v14   KAKGAVEHVVKKVVKSVVPIKQKGDQPSEAAVEETVPSGDSAETEFEVPEEQYVDAVTTQEVNSEKVDADDAGNAE  450
p58v13   KAKGAVEHVVKKVVKSVVPIKQKGDQPSEAAVEETVPSGDSAETEFEVPEEQYVDAVTTQEVNSEKVDADDAGNAE  450
         ******..***..+*·················*·*·*****··*·*·******+++··*.· p58v 7   SQYNSDREND---EDSSDESAYETAPESLD     442
p58v 9   SQYNSDREND---EDSSDESAYETAPESLD     442
p58v14   TQQLPDAENEVRADDPKNEDSSSSSDDSDA     480
p58v13   TQQLPDAENEVRADDPKNEDSSSSSDDSDA     480
         *.+*+.+.·*···*·***.**+*****+*·+*
```

Figure 4B

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1962 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: BABESIA BIGEMINA
        ( B ) STRAIN: JG-29
        ( C ) INDIVIDUAL ISOLATE: MEXICO
        ( G ) CELL TYPE: MEROZOITE ( v i i ) IMMEDIATE SOURCE:
        ( B ) CLONE: pBbg58

( i x ) FEATURE:
        ( A ) NAME/KEY: CDS
        ( B ) LOCATION: 186..1628

( i x ) FEATURE:
        ( A ) NAME/KEY: sig_peptide
        ( B ) LOCATION: 186..248

( i x ) FEATURE:
        ( A ) NAME/KEY: polyA_site
        ( B ) LOCATION: 1884..1889

( x i ) SEQUENCE DESCRIPTION: SEQ ID NO:1:

```
TATGGCACAT TGGCGCATAA GCACTCCCAA TAAGTGATTG TGAACGCGGA ATTAGGTCGG              60

CCGTGCCGTT TTTCCGTTAG AATAATATTT CAAGCAGATT CGTCTAATCG TTCTGCTGTC            120

ACTATCGTAA TACACATAGC GTTGTCTGCT AACGTTTTGT GAGCAACATT CCCATTGCG             180

TAACA ATG AGG AGC TTC TTG GGT GTG TGT TTT GGA GCT CTC TTG CTC                227
      Met Arg Ser Phe Leu Gly Val Cys Phe Gly Ala Leu Leu Leu
      1             5                       10

GTA GCA AGG AGC GGT TCT GCT ATT CGC TAT ACT CAC CGT TCG GGT GTT              275
Val Ala Arg Ser Gly Ser Ala Ile Arg Tyr Thr His Arg Ser Gly Val
15              20                  25                  30

ATG TCA GCA GAG GTG GTT GGA GAT GTG TCC AAG ACC TTG CTG GAA GCC              323
Met Ser Ala Glu Val Val Gly Asp Val Ser Lys Thr Leu Leu Glu Ala
                35                  40                  45

AAT GAG GTT GTC AAT GCT GAA ATG GAA GCA ACT CAG GTC AAC AAA GAT              371
Asn Glu Val Val Asn Ala Glu Met Glu Ala Thr Gln Val Asn Lys Asp
            50                  55                  60

ATG CAA AGT CAA TTG TCT AAT GTT AAG GAG ACC ATT GTT GGT GAG GTC              419
Met Gln Ser Gln Leu Ser Asn Val Lys Glu Thr Ile Val Gly Glu Val
        65                  70                  75

TGC GAG AAA GTT GCT GGA AAC TCT ACC TGC GGT GAG AGC GTA ATT GCC              467
Cys Glu Lys Val Ala Gly Asn Ser Thr Cys Gly Glu Ser Val Ile Ala
    80                  85                  90

TAT GTT AAC CGT TGT GAT GAG GGC GAT TGT CTG ACG CTT GAC AGC ATG              515
Tyr Val Asn Arg Cys Asp Glu Gly Asp Cys Leu Thr Leu Asp Ser Met
95                  100                 105                 110

AAG TAC AAG CCG TTG AGT CTG CCA AAT CCT TAC CAG TTG GAC GCT GCC              563
Lys Tyr Lys Pro Leu Ser Leu Pro Asn Pro Tyr Gln Leu Asp Ala Ala
                115                 120                 125

TTC ATG CTT TTC AGG GAA AGT GAT TCT AAC CCT GCG AAG AAT GAG GTG              611
Phe Met Leu Phe Arg Glu Ser Asp Ser Asn Pro Ala Lys Asn Glu Val
            130                 135                 140

AAG CGC TTC TGG ATG CGT TCG AGG AGC AGC CAC GGC GAC TAC CAT CAC              659
Lys Arg Phe Trp Met Arg Ser Arg Ser Ser His Gly Asp Tyr His His
        145                 150                 155

TTT GTT GTT AGC TTG TTG AAG AAG AAT GTT GTA CGC GAC CCT GAA TCC              707
Phe Val Val Ser Leu Leu Lys Lys Asn Val Val Arg Asp Pro Glu Ser
    160                 165                 170

AAT GAT GTT GAG AAC TTC GCA TCG CAG TAC TTC TAC ATG ACT ACG TTG              755
Asn Asp Val Glu Asn Phe Ala Ser Gln Tyr Phe Tyr Met Thr Thr Leu
175                 180                 185                 190

TAC TAC AAG ACT TAC CTG ACC GTT GAC TTT ACG GCG GCT AAG TTC TTC              803
Tyr Tyr Lys Thr Tyr Leu Thr Val Asp Phe Thr Ala Ala Lys Phe Phe
                195                 200                 205

AAC AAG CTT GCT TTC ACA ACT CGC CTG TTC GGT TTC GGT ATC CAG AAG              851
Asn Lys Leu Ala Phe Thr Thr Arg Leu Phe Gly Phe Gly Ile Gln Lys
            210                 215                 220

GCG TTG AAG CGT TTG GTT AGG AGC AAC CTT CCC GTT GAC CTT GGA ACC              899
Ala Leu Lys Arg Leu Val Arg Ser Asn Leu Pro Val Asp Leu Gly Thr
        225                 230                 235

CAC CCT GAG GCC ACC ATC CGC GAA ATA GCT AGC GGC TAC GGC GAG TAC              947
His Pro Glu Ala Thr Ile Arg Glu Ile Ala Ser Gly Tyr Gly Glu Tyr
    240                 245                 250

ATG ATG ACC CAG GTG CCT GCG ATG ACC TCG TTC GCT GAG CGT TTC TCC              995
Met Met Thr Gln Val Pro Ala Met Thr Ser Phe Ala Glu Arg Phe Ser
255                 260                 265                 270

AAG ATG GCT ACT AAG ACT CTG TTG GTT ACC GTC AGC GAC TAC GTC CAT             1043
Lys Met Ala Thr Lys Thr Leu Leu Val Thr Val Ser Asp Tyr Val His
                275                 280                 285

TTG CCC GCG TAC AAG AGG TGG TAC AGG AAG TTC AAG GAA TTC ATT GTG             1091
Leu Pro Ala Tyr Lys Arg Trp Tyr Arg Lys Phe Lys Glu Phe Ile Val
            290                 295                 300
```

```
AAC TTC TTT ACT GAC CCT GCC AAG TTG ATT ATG AAG CAC GTC TCT CAG    1139
Asn Phe Phe Thr Asp Pro Ala Lys Leu Ile Met Lys His Val Ser Gln
        305             310             315

CCT GTA AAG ACT GCC TAC ACA AAG CTG GTC CCC GAA GAG CAC AGG CAG    1187
Pro Val Lys Thr Ala Tyr Thr Lys Leu Val Pro Glu Glu His Arg Gln
    320             325             330

GCT ATC AGG AAT GTC GTC GGT CAA AGC ACC AAG CAT ATT GCC AAC GGT    1235
Ala Ile Arg Asn Val Val Gly Gln Ser Thr Lys His Ile Ala Asn Gly
335             340             345             350

GTA CGT GAT TTG TCA AGG ATG ATT AAG GAG CCT AGC CAA CAA ATA ATT    1283
Val Arg Asp Leu Ser Arg Met Ile Lys Glu Pro Ser Gln Gln Ile Ile
                355             360             365

CGT GAG AAG CTG CCT CAC TAC CTT TCT AAG GCA AAG GGA GCC GTT GAG    1331
Arg Glu Lys Leu Pro His Tyr Leu Ser Lys Ala Lys Gly Ala Val Glu
        370             375             380

CAC GTT GTT AAG AAG GTT AAA TCC GTT GTG CCG ATA AAG CAA AAG GGC    1379
His Val Val Lys Lys Val Lys Ser Val Val Pro Ile Lys Gln Lys Gly
            385             390             395

GAC CAA CCA TCC GAA GCA GCT GTA GAG GAA ACC GTT CCG TCT GGC GAT    1427
Asp Gln Pro Ser Glu Ala Ala Val Glu Glu Thr Val Pro Ser Gly Asp
        400             405             410

TCC GCG GAA ACT GAA TTT GAG GTC CCT GAA GAA CAA TAC GTC GAT GCT    1475
Ser Ala Glu Thr Glu Phe Glu Val Pro Glu Glu Gln Tyr Val Asp Ala
415             420             425             430

GTT ACT ACT CAG GAG GTT AAC AGC GAG AAG GTT GAT GCC GAC GAT GCG    1523
Val Thr Thr Gln Glu Val Asn Ser Glu Lys Val Asp Ala Asp Asp Ala
                435             440             445

GGT AAT GCC GAA ACC CAG CAG CTT CCA GAT GCA GAA AAT GAA GTG CGC    1571
Gly Asn Ala Glu Thr Gln Gln Leu Pro Asp Ala Glu Asn Glu Val Arg
            450             455             460

GCT GAT GAC CCC AAA AAT GAA GAT TCT TCA AGT TCT TCA GAT GAT TCA    1619
Ala Asp Asp Pro Lys Asn Glu Asp Ser Ser Ser Ser Ser Asp Asp Ser
        465             470             475

GAT GCG                 TAACAGCAAT TTAGCTGTAC ATTTCGATAG TGTTGCTGTC AAATAATCGC   1675
Asp Ala
480

CATATAACAA TTTCGAATGC CTAATCTCCA TCGTTTTTTA CTTTTATGTT GGTCAGGTGT              1735

TCATATTTGC CAAGGCACCG TGCTGAGATC GCTGCGTCAT TTTTGCGTGT AATATGTCGT              1795

ATAATATGCG TCCCATGGCT GCGCTGCTAT TCGCTACATG CGCTGCCAAC ATGGCCGTAG              1855

ATAGCGTGTC TGCAGGCAAC GCTGCAATAA TAAAAAATGT CGTGACTGAG TTACGCACGC              1915

GCCATAACGT TATACAATCA GTATTAGAAG AGTACAGCGT CGACTGC                            1962
```

( 2 ) INFORMATION FOR SEQ ID NO:2:

( i ) SEQUENCE CHARACTERISTICS:
        ( A ) LENGTH: 480 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Arg Ser Phe Leu Gly Val Cys Phe Gly Ala Leu Leu Leu Val Ala
 1               5                  10                  15

Arg Ser Gly Ser Ala Ile Arg Tyr Thr His Arg Ser Gly Val Met Ser
            20                  25                  30

Ala Glu Val Val Gly Asp Val Ser Lys Thr Leu Leu Glu Ala Asn Glu
        35                  40                  45

Val Val Asn Ala Glu Met Glu Ala Thr Gln Val Asn Lys Asp Met Gln
    50                  55                  60
```

-continued

| | | | | | | | | | | | | | | |
|---|---|---|---|---|---|---|---|---|---|---|---|---|---|---|
| Ser | Gln | Leu | Ser | Asn | Val | Lys | Glu | Thr | Ile | Val | Gly | Glu | Val | Cys | Glu |
| 65 | | | | | 70 | | | | 75 | | | | | | 80 |
| Lys | Val | Ala | Gly | Asn | Ser | Thr | Cys | Gly | Glu | Ser | Val | Ile | Ala | Tyr | Val |
| | | | | 85 | | | | | 90 | | | | | 95 | |
| Asn | Arg | Cys | Asp | Glu | Gly | Asp | Cys | Leu | Thr | Leu | Asp | Ser | Met | Lys | Tyr |
| | | | 100 | | | | | 105 | | | | | 110 | | |
| Lys | Pro | Leu | Ser | Leu | Pro | Asn | Pro | Tyr | Gln | Leu | Asp | Ala | Ala | Phe | Met |
| | | | 115 | | | | 120 | | | | | 125 | | | |
| Leu | Phe | Arg | Glu | Ser | Asp | Ser | Asn | Pro | Ala | Lys | Asn | Glu | Val | Lys | Arg |
| | 130 | | | | | 135 | | | | | 140 | | | | |
| Phe | Trp | Met | Arg | Ser | Arg | Ser | Ser | His | Gly | Asp | Tyr | His | His | Phe | Val |
| 145 | | | | | 150 | | | | | 155 | | | | | 160 |
| Val | Ser | Leu | Leu | Lys | Lys | Asn | Val | Val | Arg | Asp | Pro | Glu | Ser | Asn | Asp |
| | | | | 165 | | | | | 170 | | | | | 175 | |
| Val | Glu | Asn | Phe | Ala | Ser | Gln | Tyr | Phe | Tyr | Met | Thr | Thr | Leu | Tyr | Tyr |
| | | | | 180 | | | | | 185 | | | | 190 | | |
| Lys | Thr | Tyr | Leu | Thr | Val | Asp | Phe | Thr | Ala | Ala | Lys | Phe | Phe | Asn | Lys |
| | | 195 | | | | | 200 | | | | | 205 | | | |
| Leu | Ala | Phe | Thr | Thr | Arg | Leu | Phe | Gly | Phe | Gly | Ile | Gln | Lys | Ala | Leu |
| | 210 | | | | | 215 | | | | | 220 | | | | |
| Lys | Arg | Leu | Val | Arg | Ser | Asn | Leu | Pro | Val | Asp | Leu | Gly | Thr | His | Pro |
| 225 | | | | | 230 | | | | | 235 | | | | | 240 |
| Glu | Ala | Thr | Ile | Arg | Glu | Ile | Ala | Ser | Gly | Tyr | Gly | Glu | Tyr | Met | Met |
| | | | | 245 | | | | | 250 | | | | | 255 | |
| Thr | Gln | Val | Pro | Ala | Met | Thr | Ser | Phe | Ala | Glu | Arg | Phe | Ser | Lys | Met |
| | | | 260 | | | | | 265 | | | | | 270 | | |
| Ala | Thr | Lys | Thr | Leu | Leu | Val | Thr | Val | Ser | Asp | Tyr | Val | His | Leu | Pro |
| | | 275 | | | | | 280 | | | | | 285 | | | |
| Ala | Tyr | Lys | Arg | Trp | Tyr | Arg | Lys | Phe | Lys | Glu | Phe | Ile | Val | Asn | Phe |
| | 290 | | | | | 295 | | | | | 300 | | | | |
| Phe | Thr | Asp | Pro | Ala | Lys | Leu | Ile | Met | Lys | His | Val | Ser | Gln | Pro | Val |
| 305 | | | | | 310 | | | | | 315 | | | | | 320 |
| Lys | Thr | Ala | Tyr | Thr | Lys | Leu | Val | Pro | Glu | Glu | His | Arg | Gln | Ala | Ile |
| | | | | 325 | | | | | 330 | | | | | 335 | |
| Arg | Asn | Val | Val | Gly | Gln | Ser | Thr | Lys | His | Ile | Ala | Asn | Gly | Val | Arg |
| | | | 340 | | | | | 345 | | | | | 350 | | |
| Asp | Leu | Ser | Arg | Met | Ile | Lys | Glu | Pro | Ser | Gln | Gln | Ile | Ile | Arg | Glu |
| | | 355 | | | | | 360 | | | | | 365 | | | |
| Lys | Leu | Pro | His | Tyr | Leu | Ser | Lys | Ala | Lys | Gly | Ala | Val | Glu | His | Val |
| | 370 | | | | | 375 | | | | | 380 | | | | |
| Val | Lys | Lys | Val | Lys | Ser | Val | Val | Pro | Ile | Lys | Gln | Lys | Gly | Asp | Gln |
| 385 | | | | | 390 | | | | | 395 | | | | | 400 |
| Pro | Ser | Glu | Ala | Ala | Val | Glu | Glu | Thr | Val | Pro | Ser | Gly | Asp | Ser | Ala |
| | | | | 405 | | | | | 410 | | | | | 415 | |
| Glu | Thr | Glu | Phe | Glu | Val | Pro | Glu | Glu | Gln | Tyr | Val | Asp | Ala | Val | Thr |
| | | | 420 | | | | | 425 | | | | | 430 | | |
| Thr | Gln | Glu | Val | Asn | Ser | Glu | Lys | Val | Asp | Ala | Asp | Ala | Gly | Asn |
| | | 435 | | | | | 440 | | | | | 445 | | | |
| Ala | Glu | Thr | Gln | Gln | Leu | Pro | Asp | Ala | Glu | Asn | Glu | Val | Arg | Ala | Asp |
| | 450 | | | | | 455 | | | | | 460 | | | | |
| Asp | Pro | Lys | Asn | Glu | Asp | Ser | Ser | Ser | Ser | Asp | Asp | Ser | Asp | Ala |
| 465 | | | | | 470 | | | | | 475 | | | | | 480 |

IMMUNIZATION AGAINST BABESIOSIS USING PURIFIED SURFACE ANTIGENS OF BABESIA BIGEMINA AND SIMILAR IMMUNOGENS

Cross-Reference to a Related Application

This application is a continuation-in-part of co-pending application Ser. No. 07/663,255, filed Mar. 1, 1991, now U.S. Pat. No. 5,209,929, which is a continuation of application Ser. No. 07/031,328, filed Mar. 27, 1987, now abandoned.

TECHNICAL FIELD

This invention relates to the immunization of cattle and other animals subject to infection by protozoan species of Babesia.

BACKGROUND OF THE INVENTION

Bovine babesiosis is an intraerythrocytic protozoan disease of cattle caused by Babesia bigemina, Babesia bovis, Babesia major, Babesia divergens, and Babesia jakirnovi. These parasites have antigenie similarities and differences that may have important functional roles in the induction of protective immunity and antibody-based diagnosis. Also, B. boris isolates, including the current Australian vaccine strain, are now known to consist of subpopulations that vary antigenically, in virulence, and in abundance within an isolate (Cowman, A. F., P. Timms, and D. J. Kemp [1984]Mol. Biochem. Parasitol. 11:91-103; Gill, A. C., A. F. Cowman, N. P. Stewart, D. J. Kemp, and P. Timms [1987]Exp. Parasitol. 63:180-188). Other mammals may also be subject to infection by species of Babesia. The disease is enzootic to tropical and subtropical climates where it poses severe constraints on livestock production. The risk of the disease and losses caused by it restrict movement of cattle to and from such enzootic regions. This restricted movement results in the loss of opportunities to upgrade local herds by importation of genetically superior breeds susceptible to the disease. Though some degree of immunity has been shown to develop following natural infection (Hall, W. J. K. et al. [1968] Aust. Vet. J. 44:259-264; Mahoney, D. F. et al. [1973] Annals Trop. Med. and Parasit. 67:197-203), significant losses of cattle, meat, and milk production still result from babesiosis induced by Babesia bigemina.

The infective form of Babesia bigemina is the sporozoite which is found in the salivary gland of infected Boophilus microplus and possibly other species of Boophilus ticks. After being introduced into the tissues of the bovine host by the bite of a tick, the sporozoites enter red blood cells (erythrocytes) of the host animal. The sporozoites multiply and develop into merozoites within the erythrocytes. Infection initiates a cycle of host erythrocyte invasion and lysis that results in the clinical disease, babesiosis, which can often result in the death of the host. Recovery from acute babesiosis is associated with immunological response including development of long lasting protective immunity against subsequent challenge.

Despite many years of research relating to babesiosis, effective practical vaccines or other immunoprophylaxes against Babesia bigemina induced babesiosis are not available to the herdsman. The most common vaccination practice in use today is premunition, which is the inoculation of susceptible animals with blood infected with parasites which have been rendered less virulent (Callow, L. L. [1977] "Immunity to Blood Parasites of Animals and Man," In Vaccination Against Bovine Babesiosis, Plenum Press, NY, pp. 121; Dalgliesh, R. J. et al. [1981] Aust. Vet. J. 57:8-11). Although premunition provides good immunity against both homologous and heterologous strain challenge, it has a number of drawbacks, including: (a) induction of a carrier state which perpetuates the protozoan life cycle in the environment; (b) variation in the vaccine virulence which results in death, abortion, or clinical disease in some vaccinates; (c) contamination of the inoculant with other blood-borne infectious agents such as bovine leukosis virus, bluetongue virus, anaplasma, and theileria; (d) cumbersome and expensive production, storage, and transport procedures which render vaccination impractical in many parts of the world; and (e) contamination of the vaccinates with host erythrocytes. Various experimental vaccines using inactivated Babesia parasites only provide partial protection against homologous strain challenge and poor protection against heterologous strain challenge.

Some specific immunogens of Babesia bovis merozoites have been identified and characterized (Smith, R. D., M. A. James, M. Ristic, M. Aikawa, and C. A. Vega Y Murgula [1981] Science 212:335-338; Wright, I. G., M. White, P. O. Tracey-Patte, R. A. Donaldson, B. V. Goodger, D. J. Waltisbuhl, and D. F. Mahoney [1983] Infect. Immun. 41:244-250; Wright, I. G., G. B. Mirre, K. Rode-Bramanis, M. Chamberlain, B. V. Goodger, and D. J. Mahoney [1985] Infect. Immun. 48:109-113; Commins, M. A., B. V. Goodger, and I. G. Wright [1985] Int. J. Parasitol. 15:491-495; Waltisbuhl, D. J., B. V. Goodger, I. G. Wright, G. B. Mirre, and M. A. Commins [1987] Parasitol Res. 73:319-323; Montenegro-James et al. [1987] Parasitol. Res. 74:142-150; Goodger et al. [Int. J. Parasitol. 17:935-940; Goodger et al. Int. J. Parasitol. 15:175-179; Goff W. L., W. C. Davis, G. H. Palmer, T. F. McElwain, W. C. Johnson, J. F. Bailey, T. C. McGuire [1988] Infect. Immun. 56:2363-2368) as well as the merozoite immunogens of Babesia bigemina (McElwain, T. F., L. F. Perryman, W. C. Davis, and T. C. McGuire [1987] J. Immunol. 138(7):2298-2304; Callow, L. L. et al. [1974] Aust. Vet. J. 50:12-15; Kuttler, K. L. et al. [1980]Am. J. Vet. Res. 41:536-538; Montenegro-James et al. [1987] Parasitol. Res. 74:142-150; Figueroa et al. [1990]Parasitology 100(pt. 2):161-175; Figueroa and Buening [1991] J. Clin. Micro. 29:997-1003). However, in only one instance (Smith et al., 1981) were antigens which provided protection against infection determined to be surface-exposed on merozoites as opposed to cytoplasmic in location.

Current vaccine strategies include the use of attenuated live Babesia bovis parasites (Callow et al. [1979] Int. J. Parasitol. 9:333-338) and various inactivated preparations (Montenegro-James, S., M. Toro Benitez, E. Leon, R. Lopez, and M. Ristic [1987] Parasitol. Res. 74:142-150; Smith et al., 1981; U.S. Pat. No. 4,762,711 issued to Buening et al.; Kuttler, K. L., M. G. Levy, M. A. James, M. Ristic [1982] Am. J. Vet. Res. 43(2):281-284; Kuttler, K. L. et al. [1983] Am. J. Vet. Res. 44:1456-1459). Protection of cattle against B. bovis has been compared using commercial B. bovis vaccines, live parasites, or non-living supernatant antigens (Timms, P. et al. [1983] Aust. Vet. J. 60:75-77). The attenuated vaccine provides the best protection against challenge with both homologous and heterologous strains, although there are a number of serious disadvantages, including a short shelf-life, variation in virulence, contamination with host erythrocyte stroma, and perpetuation of the life cycle by creation of a carrier state. Inactivated vaccines induce protection against challenge with homologous strains; however, only partial protection occurs against challenge with heterologous strains. In addition, with the exception of Montenegro-James et al., these vaccine strategies have been directed solely to protection against babesiosis induced from *B. bovis* strains.

Animals that survive natural field infection or that recover from infection with an attenuated vaccine strain are protected against clinical disease. However, premunization in this manner is expensive, impractical in developing countries that lack the necessary infrastructure, and a potential mode of transmission for other blood-borne diseases.

There remains a need to overcome the known disadvantages of prior art vaccines by developing vaccines and methods for preventing or minimizing the pathological effects of *Babesia bigemina* induced babesiosis.

BRIEF SUMMARY OF THE INVENTION

Disclosed and claimed here are novel merozoite proteins of *Babesia bigemina*. These proteins are known to be expressed on the surface of the merozoite and may be used to raise neutralizing antibodies. Thus, they can be used in the formulation of subunit vaccines for the prophylaxis of bovine babesiosis. Advantageously, one peptide has been discovered which can raise antibodies to both *Babesia bigemina* and *Babesia boris*, while others are species, or even isolate, specific.

Also disclosed are monoclonal antibodies to bovine babesiosis antigens. These monoclonal antibodies are used to identify merozoite surface antigens and may be used in the treatment and/or diagnosis of bovine babesiosis.

A further element of the invention is the identification of genes which code for *Babesia* proteins. These genes can be used to make recombinant proteins which can be utilized for vaccines.

The invention also provides a means of detecting the presence of disease-causing *Babesia* organisms. The detection method involves the use of DNA probes which selectively identify the presence of these organisms. The method of detection can be incorporated into kits comprising various disclosed elements for use in diagnostic or other such assays.

BRIEF DESCRIPTION OF THE SEQUENCES

Sequence 1 is the DNA sequence and translated amino acid sequence of p58.

Sequence 2 is the 480 amino acid sequence of p58.

BRIEF DESCRIPTION OF THE DRAWING

FIG. 1 is a comparison of the blocks containing amino acids 1 to 307 of p58 from *B. bigemina* and 1 to 319 of Bv60 from *B. bovis*. Cysteine residues are underlined. Displayed are the symbols "." between residues whose comparison value is greater than or equal to 0.1 or ":" when it is greater than or equal to 0.5. A vertical bar "|" denotes identity among residues. The symbol ". . . ." denotes a gap used to achieve optimal alignment between the two polypeptide sequences.

FIG. 2A-2E is a comparison of the nucleotide sequences encoding p58 genes deduced from sequence analysis of the plasmid clones. Dot (.), star (*), and plus (+) signs represent perfectly conserved, well-conserved, and non-conserved substitution, respectively. The 5' and 3' non-coding sequences are depicted in lower case letters. The initiation codon (ATG) and the termination codon (TAA) are underlined. The "Clustal" program of Higgins and Sharp (Higgins, D. G., R. M. Sharp [1988] Gene 73:237-294) was used to align the four sequences. Gaps (−) were introduced to compensate for length and for optimal alignment.

FIG. 4A–4B is a comparison of the complete amino acid sequences deduced from the ORFs of each of the *B. bigemina* p58 gene copies. Explanation of characters is provided in the legend for FIG. 2. The alignment was done using the "Clustal" program described by Higgins and Clark, supra.

DETAILED DESCRIPTION OF THE INVENTION

Figure 3:
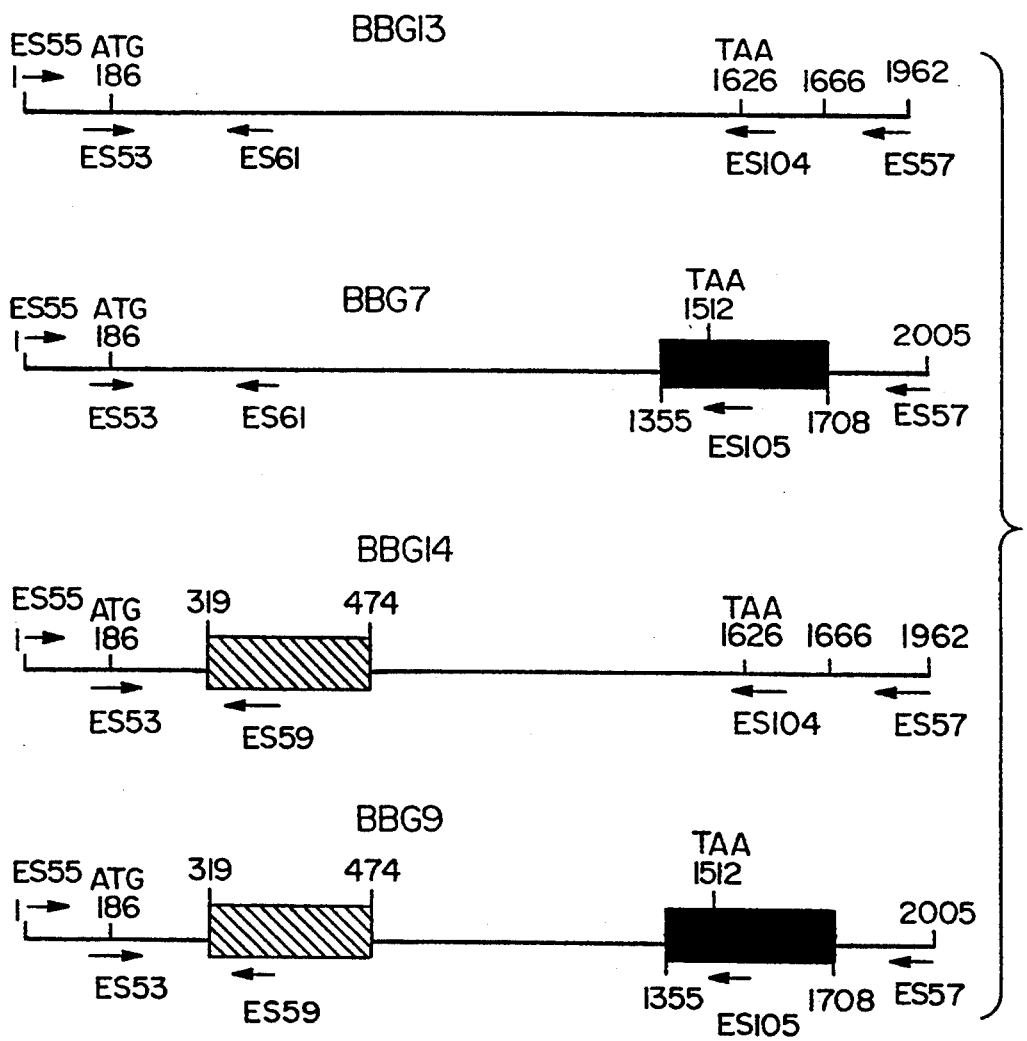
FIG. 3 is a schematic representation of Bbg7, Bbg9, Bbg13, and Bbg14 gene copies of the p58 multigene family. Shown are the locations of the initiation codon (ATG), termination codon (TAA), and regions of 5' (hatched box) and 3' (dark box) sequence variation. Arrows indicate the positions of different primers.

Inoculants and vaccines according to this invention include substantially pure antigenic surface proteins derived from or patterned after the merozoite stage of *Babesia bigemina*. The surface proteins useful in this invention must be capable of stimulating at least some significant immune response in the cattle or other susceptible animals being treated. The inventive immunogenic surface proteins thus have both antigenic and immunogenic effects when inoculated into the animal being treated.

The substantially pure proteins useful in this invention are advantageously identified by purifying *Babesia bigemina* merozoites from infected blood of an animal of the same species as those to be treated. This is preferably done by gradient separation of the merozoites from host erythrocytes and other blood cells and structures. This is advantageously accomplished by washing infected blood with buffer solutions, subjecting to centrifugation, and by selectively removing predominantly merozoite fractions from the gradient solutions, as described more fully hereinafter. The isolated predominantly viable merozoites are then used to generate monoclonal antibodies used to discriminate the inventive immunogenic merozoite proteins from non-immunogenic proteins which also exist in the merozoite cells.

The monoclonal antibodies are prepared by first vaccinating mice with the viable *Babesia bigemina* merozoites. Lymphocytes from the spleen of the infected mice are then obtained and fused with myeloma cells using polyethylene glycol or other appropriate cell fusing agent, to produce fused cell hybridomas. The hybridomas and their clones produce monoclonal antibodies to various antigens contained in the *Babesia bigernina* used to infect the mice.

Monoclonal antibodies from the hybridomas or their clones are then initially screened to determine which antibodies bind to surface reactive epitopes of the merozoites, such as by using indirect immunofluorescent assay of *Babesia bigemina* infected blood with both fixed and viable merozoites. The monoclonal antibodies which bind to the surface of the live merozoites are then further screened for reactivity using radioisotope-labeled surface proteins free from the merozoites. Some of these labeled surface proteins are selectively immunoprecipitated by some of the surface-reactive monoclonal antibodies identified in the immunofluorescent assays.

The immunoprecipitated antigenic surface proteins are further analyzed to determine their molecular weight using gel electrophoresis. The molecular weights of the surface proteins immunoprecipitated by the monoclonal antibodies are then further compared and analyzed to determine the number and molecular weights of those which have surface reactive epitopes. The antigenic merozoite surface proteins are preferably further analyzed to determine which are reactive to antibodies raised in immune animals which have been infected and recovered from babesiosis caused by *B. bigemina*. This further discrimination is advantageously accomplished using immunoprecipitation of radioisotope-labeled merozoite proteins by immune sera collected from such animals. The resulting identified antigenic surface proteins can then be isolated into a purified form.

Hybridoma cell lines are used to produce the monoclonal antibodies which selectively bind to the desired proteins. The selected monoclonal antibodies can then be used to remove the desired antigenic proteins from infected blood using an immunoaffinity chromatography column or similar immunoaffinity or immunoprecipitation techniques.

Purified monoclonal antibodies most desirable for use in immunoaffinity chromatography are advantageously produced by collection of ascitic fluid from mice vaccinated with the corresponding hybridomas or clones which produce the desired monoclonal antibodies. The collected ascitic fluid is then purified, such as by precipitation and chromatography as described below. Each purified monoclonal antibody is then advantageously coupled to an insoluble matrix such as Sepharose to prepare an immunoaffinity matrix. Partially purified disrupted *Babesia bigemina* merozoites are then passed through the immunoaffinity matrices, and the desired merozoite proteins are selectively adsorbed onto the individual monoclonal antibodies held by each matrix. The non-adsorbed materials are washed through the affinity chromatography column and the desired proteins recovered from the affinity chromatography column matrix, such as explained more fully below.

In research related to cattle, five monoclonal antibodies resulted in identification of at least five major immunoprecipitated merozoite surface proteins having apparent molecular weights of 36, 45, 55, 58, and 72 kilo-daltons (kDa). Such immunogenic proteins are herein identified as gp36, gp45, gp55, p58, and p72, respectively. Each of the above surface proteins is identified by its highest molecular weight component consistently present in both immunoprecipitates and affinity chromatograph eluates, preceded by the letters "p" or "gp." Four of the five *B. Bigemina* merozoite proteins with surface-exposed epitopes were further characterized as to size, epitope conservation among isolates, and post-translational modification. Each of them can be purified by immunoaffinity chromatography in quantities sufficient for immunizing cattle. gp45, gp55, and p58 can be used to induce an immune response that neutralizes merozoites, reducing the peak level of parasitemia in experimentally challenged cattle. Some of the monoclonal antibodies also immunoprecipitated secondary merozoite proteins. The additional proteins bound by the monoclonal antibodies were also present in the vaccines tested and may also be immunogenic.

Monoclonal antibodies identified herein as 14.1, 14.20, and 14.16 bound to such antigenic proteins, respectively. Four hybridoma cell lines survived cloning. Such cell lines produce monoclonal antibodies 14.1, 14.16, 14.20, and 14.52, and were deposited with the American Type Culture Collection, 12301 Parklawn Drive, Rockville, Md. 20852 and were assigned the accession numbers HB 9377, HB 9379, HB 9376, and HB 9378, respectively.

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposits should the depository be unable to furnish a sample when requested, due to the condition of a deposit. All restrictions on the availability to the public of the subject culture deposits will be irrevocably removed upon the granting of a patent disclosing them.

The degree of purity of proteins useful in accordance with the present invention is much higher than the purity of the surface antigen in its natural state. As an example, in its natural state p58 is believed to be present in an amount of about 0.01 to 0.1% of the total protein present in the merozoites. In its natural state, many other impurities such as about 100–200 other proteins, carbohydrates, glycoproteins, and nucleic acids are present. However, the p58 protein can be purified to a purity of at least 90 weight percent, preferably at least 95 weight percent, and most preferably at least 98 weight percent. The purified p58 includes a primary protein having an approximate molecular weight of about 58,000 daltons and variably three secondary proteins having approximate molecular weights of 36, 35, and 33 kDa. The p58 is essentially free of contaminating proteins, glycoproteins, carbohydrates, nucleic acids, and most other contaminating antigens. Similar relationships are believed to exist with respect to other immunogenic proteins or protein combinations according to this invention.

The discovered immunogenic surface proteins are also polypeptides. An active fragment or combination of fragments of these polypeptides may be effective in inducing immunity to *Babesia bigemina* in cattle and possibly other affected animals. The size of the active fragment may be as small as about six to ten amino acids.

The purified immunogenic surface antigens or an active fragment thereof may be produced by immunoaffinity chromatography or polypeptide synthesis. Preferably, the purified immunogenic surface antigen or an active fragment thereof can be produced by genetic engineering (DNA cloning with protein fragment expression). The gene encoding the conserved, neutralization sensitive surface protein p58 of Babesia bigemina was cloned and sequenced (SEQ. ID 1). An open reading frame of 1440 bases was found to encode a protein with a predicted molecular weight of 54 kDa. Four gene copies were present in the biologically cloned Mexico strain of B. bigemina from which the cDNA clone was derived. A transmembrane hydrophobic domain and signal peptide were present at the amino-terminus. The polypeptide encoded by a nearly full length cDNA was expressed in bacteria and contained epitope(s) reactive with anti-p58 polyclonal and monoclonal antibodies. Serum antibodies from rabbits immunized with a lysate of recombinant bacteria specifically immunoprecipitated native p58 from 35S-methionine labeled B. bigemina antigens. In addition, the sera contained antibodies that bound to the surface of live merozoites from four geographically different Latin America isolates, confirming the presence and immunogenicity of conserved, surface exposed epitopes on the recombinant polypeptide. This molecular clone will now enable immunization in cattle to induce immune protection. The cattle may be vaccinated with the full length p58 protein or an immunologically active fragment thereof.

Recombinant phage expressing a protein reacting with antibodies in monospecific anti-p58 rabbit serum (R931) was isolated from a cDNA library prepared from B. bigemina poly-A selected RNA. Restriction enzyme analysis of recombinant plasmid (pBbg58) excised from the lambda Zap II vector revealed an insert with a size of approximately 1.5 kilobases. Immunoblotting of bacterial lysate expressing pBbg58 demonstrated the presence of recombinant proteins (designated rp58) migrating at 68 and 53 kDa apparent molecular weight that were reactive with both monoclonal antibody 14/16.1.7 and R931 antibodies against native p58. Several smaller molecular weight polypeptides were also detected with 14/16.1.7. Control E. coli expressing an irrelevant 0.8 kb insert (Stratagene Inc., La Jolla, Calif.) was unreactive with 14/16.1.7 or R931 serum. None of the rp58 polypeptides reacted with a control rabbit serum or a control monoclonal antibody.

The immunogenicity of rp58 was tested by immunizing rabbits with lysates of E. coli expressing either pBbg58 or an irrelevant control insert. Anti-recombinant p58 rabbit serum immunoprecipitated native p58 from $^{35}$S-methionine labeled B. bigemina proteins, and bound to the surface of live, gradient separated merozoites from four geographically different Latin American isolates (Mexico, Texcoco, St. Croix, and Puerto Rico). Control monoclonal antibody and rabbit preimmune serum, and immune serum from a rabbit immunized with the control insert were unreactive with the 58 kDa antigen and did not bind to the merozoite surface.

The complete nucleotide sequence of the gene encoding p58 was determined by sequencing the cDNA insert (1483 bases) and part of a genomic clone (bases 1-192 and 1676-1962) isolated from a lambda GEM11 library using a $^{32}$P-labeled pBbg58 probe. The DNA sequence and its translated amino acid sequence are shown in SEQ. ID 1. The total sequence of 1962 bp contains a long open reading frame extending from an initiation ATG codon at position 186-188 to a termination site at position 1626-1628. The ATG codon starting at position 186 is part of a consensus Kozak sequence (ACAATGA), and the upstream sequence has multiple stop codons in all three reading frames. Poly-A containing mRNA was sequenced using a reverse complement oligonucleotide binding to the sequence from bases 256 to 275. The message for p58 came to a strong stop at a point equivalent to positions 30-33 of the DNA sequence, confirming the location of the transcription start site. The short sequence downstream of the termination codon TAA at position 1626 includes an mRNA decay consensus motif ATTTA and a conventional polyadenylation signal AATAAA.

The 1440 nucleotide open reading frame encodes a protein consisting of 480 amino acid residues with a predicted molecular weight of 53,794. Computer analysis and a plot of hydrophobicity identifies a hydrophobic region starting at amino acid 3 and ending at 19 that could be used as a transmembrane anchor segment. In addition, a eukaryotic signal sequence starting from the initiation methionine and ending at amino acid 21 with a cleavage site between amino acids 21 and 22 is present.

Genomic DNA of clone JG-29 digested with EcoRI and PstI was hybridized to $^{32}$P-labeled pBbg58. Four major EcoRI fragments and two major PstI fragments hybridize to the cDNA probe, Which contains a single internal EcoRI site and no internal PstI sites. An additional faintly hybridizing fragment was present in both the EcoRI and PstI digests. All immunologic analysis to date has indicated strict antigenic conservation of p58 immunologic epitopes. As stated above, four gene copies were present in the Mexico strain from which the cDNA clone was derived.

The four gene copies encoding the merozoite surface protein p58 from the protozoan hemoparasite Babesia bigeraina were amplified from genomic DNA by polymerase chain reaction (PCR) techniques, molecularly cloned, and subjected to DNA sequence analysis. The amplified DNA was classified into two classes with respect to size. The larger sized class of DNA contained two different p58 gene copies, designated Bbg7 and Bbg9, both of which were 2005 nucleotide base pairs in length with a p58 open reading frame (ORF) that was 1326 nucleotides in length. The smaller sized class also contained two different copies of the p58 gene, Bbg13 and Bbg14, and were 1962 nucleotide base pairs in length. With the exception of a single base substitution, the sequence of Bbg13 is identical to the cDNA sequence described herein. DNA sequence analysis revealed that Bbg7 and Bbg14 gene copies of the p58 diverged from Bbg13 sequence at regions toward the 3' and 5' ends, respectively. In contrast, sequence analysis revealed that Bbg9 incorporated both regions of divergence within its sequence. Expression of mRNA from each p58 gene copy from blood stage parasites was examined. RNA-PCR and northern blot analyses demonstrate the in vivo transcription of three of the four copies, although one of the three expressed copies is present in very low abundance. The relative abundance and size of the two p58 mRNA species detected are consistent with the $M_r$ of 58,000 and 55,000 proteins detected in in vitro translation of B. bigemina poly(A+) mRNA by immunoprecipitation w/th an anti-p58 monospecific antibody. These results demonstrate that the gene encoding the p58 surface merozoite protein of B. bigemina exists as a multigene family that is differentially expressed in the blood stage of the parasite's life cycle.

Recombinant p58 expressed as a slightly truncated (missing 3 amino acids) β-galactosidase fusion protein has a predicted molecular weight of 57,000 daltons, close to that of native p58. However, rp58 expressed in E. coli contains several monoclonal antibody reactive bands, the largest two of which migrate with relative molecular weights of 68 and 53 kDa.

Significantly, as indicated by the following evidence, recombinant p58 contains conserved immunogenic epitopes present in the native protein and exposed on the surface of live merozoites: (1) it reacts with monoclonal and monospecific, polyclonal antibodies recognizing surface exposed epitopes on native p58, (2) antibodies against rp58 bind to the surface of live merozoites, and (3) antibodies against rp58 bind to the surface of merozoites from four geographically and antigenically different Latin American isolates. Although purified native p58 is highly antigenic in cattle, a relatively small portion of the antibody response is directed against the surface exposed region of the protein. Targeting the immune response toward neutralization sensitive epitopes improves protection against challenge in animals immunized with p58. We are now able to precisely identify the surface exposed and conserved regions containing these epitopes of p58 as a vaccine component.

The purified immunogenic proteins of this invention should be present in a single dose of vaccine in an amount of approximately 1–400 micrograms, preferably 5–200 micrograms, and most preferably 20–100 micrograms. A single injectable dose will usually have a volume of about 1 ml. Therefore, the concentration of purified-surface antigen in an injectable vaccine composition will usually be in the range of from about 1 to about 400 micrograms/ml, preferably about 5 to about 200 micrograms/ml, and most preferably 20–100 micrograms/ml. Immunization using alternative inoculation techniques may require substantial adjustment in the amount of active immunogen used. Immunization of non-bovines may also require such adjustment.

Vaccines according to the invention preferably include an immunogenic adjuvant such as Freund's complete adjuvant or others which are effective. The immunogenic merozoite derived surface proteins will usually be dissolved, mixed, or suspended in such an immunogenic adjuvant. The vaccine may also advantageously contain any other pharmaceutically acceptable carrier or diluent. The pharmaceutically acceptable carrier or diluent is preferably a compound, composition, or solvent which is administered as a non-toxic sterile liquid.

Methods according to the invention include inoculating animals with a vaccine or other inoculant comprising a substantially pure immunogenic surface protein, an active fragment thereof, an immunologically similar protein produced by polypeptide synthesis or genetic engineering, or a combination of such antigens. Preferably, the animals being immunized are successively vaccinated by injection with a single dose as defined above at one to six week intervals, preferably two to four week intervals, about one to five times, preferably three to five times. It would be most preferable to use one or two vaccinations in commercial applications. The substantially pure protein should be present in the vaccine in an amount effective to induce at least a partial immune response to Babesia bigemina. When the animals are subsequently challenged with virulent Babesia bigemina, the degree of acute infection is substantially reduced or even prevented. Injection will usually be performed intramuscularly (i.m.) or subcutaneously (s.c.).

The isolated immunogenic proteins, an active fragment thereof, or an immunologically analogous protein or peptide produced by polypeptide synthesis or genetic engineering can also be used as the basis of diagnostic tests, such as radioisotope, fluorescent, or enzyme linked immunosorbent assays for serologic diagnosis of babesiosis caused by B. bigemina. When blood samples from suspected animals are tested using such antigens, results distinguishing infected and non-infected animals are obtainable due to detectable levels of antibodies raised in the animal against the B. bigemina infection. Monoclonal antibodies used to selectively bind the immunogenic proteins can also be used in diagnostic kits.

Monoclonal antibodies according to this invention may be useful in treating animals acutely infected by B. bigemina. Such antibodies may be used such as by injection in the form of vaccines, using the concentrations, adjuvants, and methods described herein with respect to immunizations using the immunogenic merozoite proteins.

Immunogenic surface proteins from the intraerythrocytic merozoite stage of Babesia bigemina have been isolated using cell fusion procedures which will be discussed more fully below in the context of development of vaccines and inoculants for immunization of cattle against babesiosis from Babesia bigemina. Immunization of bovines with such isolates induces an immunological response which produces at least partial immunity which is useful in reducing the pathological effects of such disease in cattle. Production of such useful vaccines is facilitated by the isolation and determination of the DNA sequence of the genes encoding for surface active proteins on the merozoites. Comparison of the genes encoding surface active proteins between species, for example, B. bigemina and B. bovis, can identify similarities useful for exploiting in the development of vaccines against more than one species of parasite.

As used herein, the terms "substantially the same sequence" or "fragment of the sequence" refer to variations of the sequence which retain the biological activity of the specific sequences disclosed herein. For example, these "equivalent" or "fragment" sequences would include, but are not limited to, genes such as Bbg7, Bbg9, Bbg13, and Bbg14 which are disclosed herein and which are in the same gene family as p58. Other such genes could be readily located, using the teachings of the subject invention, without undue experimentation. Furthermore, it is well within the skill of a person trained in this art to make immunologically active fragments of the disclosed proteins or to make immunologically active muteins by making, for example, conservative amino acid substitutions.

Following are examples which illustrate procedures, including the best mode, for practicing the invention. These examples should not be construed as limiting. All percentages are by weight and all solvent mixture proportions are by volume unless otherwise noted.

EXAMPLE

Blood isolates from bovines infected by Babesia bigemina from Mexico, Texcoco, St. Croix, Puerto Rico, and Kenya strains of the parasite were obtained. Each isolate was stored in liquid nitrogen as a blood stabilate containing packed erythrocytes (1:1) with a cryopreservant of 10% (w/v) polyvinylpyrrolidone and 2%

(w/v) glucose in Puck's Saline G, obtainable from Gibco Laboratories of Chagrin Falls, Ohio.

A. Purification of *Babesia bigemina* Merozoites

1. Gradient Separation

The merozoites were first purified using centrifugation gradient separation in silica gel colloidal suspensions. A 20 ml stabilate of packed infected erythrocytes was thawed at 37° C. for 15 minutes, diluted to 100 ml in buffer containing 0.01M sodium phosphate, 0.15M NaCl, pH 7.2 (hereinafter PBS), and washed three times by centrifugation at 1100 G. The resulting cell pellet was suspended in 10 ml PBS and forced through a Pyrex glass wool column to remove agglutinated cells and debris. One ml aliquots of the eluate were layered on 10 ml continuous silica gel colloidal suspensions, commonly known as Percoll gradients, which were generated by centrifugation of a 40% (v/v) isosmotic solution of Percoll (Pharmacia Fine Chemicals, Uppsala, Sweden) in PBS at 30,000 G for 15 minutes. Infected erythrocyte ghosts were collected from the top of each gradient and washed 3 times in PBS by centrifugation at 2500 G. The organism was maintained at 4° C. throughout such procedure.

The objective of gradient separation purification was to obtain a purified preparation of merozoites that would facilitate the identification of surface proteins therefrom. The desired parasites were separated from other fractions of the cryopreserved blood stabilates using such processing.

2. Electron Microscopy

Electron microscopy was advantageously used to evaluate the gradient separation purification of the merozoites. Cell pellets from Percoll gradients were fixed for 1 hour in 3% (v/v) glutaraldehyde in 0.1M sodium phosphate buffer, pH 7.4. They were washed twice in 0.1M sodium phosphate buffer, pH 7.4, and treated for 1 hour in 1% (v/v) osmium tetroxide in the same buffer. Following two additional washes in said phosphate buffer, the cell pellets were dehydrated through a graded series of ethanol washes (75%, 95%, 100%), equilibrated in propylene oxide, and embedded in Epon or other plastic materials as is well known in the an using standard procedures. This sections stained with uranyl acetate and lead citrate were examined on a Hitachi 600 transmission/scanning electron microscope.

Transmission electron microscopy of the gradient separated parasites revealed both intact and disrupted merozoites. Phase micrographs of the merozoite preparation obtained 1–5 mm below the top of a 40% continuous Percoll gradient demonstrated the relative purity of the merozoites so collected at more than 95% and the absence of contaminating uninfected erythrocytes, leukocytes, and platelets.

Nearly all merozoites obtained from the Percoll gradient were surrounded by two cell membranes. Ana 13, a monoclonal antibody (IgM isotype) that reacts with an epitope on the membrane of normal bovine erythrocytes, bound to the outer membrane in indirect immunofluorescent assay (IFA) of live merozoites. Bovine immune serum against *Babesia bigemina* reacted with both membranes, but did not bind to uninfected erythrocytes. Normal bovine serum and control IgM isotype monoclonal antibody did not bind to erythrocyte or merozoite membranes in this assay.

3. Viability

The viability of the gradient separated merozoites was then tested using the following procedure: An aliquot of cells recovered from the Percoll gradients and suspended in PBS was mixed with fluorescein diacetate (hereinafter FDA) in PBS to a final concentration of 10 micrograms/ml. Following 15 minutes of incubation at room temperature, the mixture was diluted 1:100 with PBS and examined in a hemacytometer by phase and fluorescence microscopy. Viability was expressed as percentage of total cells that were fluorescent. The parasites were also subjected to various cytocidal treatments, including two freeze/thaw cycles at $-20°$ C.; 10% buffered neutral formalin treatment for 30 minutes on ice; 3% glutaraldehyde treatment for 30 minutes on ice; 0.1% saponin treatment for 15 minutes at 37° C.; or heating at 56° C. for 3 minutes; in order to confirm the dependence of FDA retention on merozoite cell membranes remaining intact.

4. Infectivity

The infectivity of the gradient separated merozoites was confirmed by intravenous inoculation of 3 splenectomized Holstein calves with $5 \times 10^7$ or $1 \times 10^8$ FDA positive parasites. The inoculated animals suffered from acute clinical babesiosis indicated by elevated rectal temperatures, decreased packed cell volume (hereinafter PCV), and parasitemia (the percentage of 100 erythrocytes containing parasites in a Wright's stained blood smear).

B. Generation of Fused Cell Hybridomas and Monoclonal Antibodies

1. Lymphocytes from Mice

Eight week old BALB/c mice were immunized subcutaneously with $1 \times 10^7$ FDA positive parasites in 0.1 ml PBS emulsified in an equal volume of complete Freund's adjuvant. Two additional booster immunizations consisting of the same number of cells in incomplete Freund's adjuvant were given subcutaneously at 10 day intervals. The mice were then immunized intravenously 3 times at 21 day intervals with $1 \times 10^7$ FDA positive cells in 0.1 ml PBS, the last immunization occurring 72 hours prior to fusion. The spleens of such immunized mice were removed for use in cell fusion.

2. Myeloma Cells

Myeloma cells were selected from a HAT (hypoxanthine, aminoterin, and thymidine)-sensitive, tissue-culture-adapted mouse myeloma cell line for use in the hybridoma cell fusions. Cells from murine myeloma cell line X-63 Ag8.653, available from the American Type Culture Collection, were used in the fusions described below.

3. Cell Fusions

Spleen cells from the mice vaccinated as described above were crushed and passed through a screen to assure division. The spleen cells were then fused with the above-described murine myeloma cells at a ratio of 2.5 nucleated spleen cells to 1 myeloma cell. The cells were fused by suspending them in a 50% aqueous solution of polyethylene glycol, such as PEG-1500, available from Baker Chemicals. The fusion took place at 25° C. for approximately 3 minutes.

The solution containing the fused cells was then diluted in serum free tissue culture medium, such as Dulbeco's Modified Eagle Medium (DMEM). Cells were then plated into 96 well microculture plates in the presence of 800,000–1,000,000 thymocytes per well and approximately 1 microgram per well of salmonella typhimurium mitogen (STM) available from Riebe Immunochem of Hamilton, Mont. Also added to the culture media was 2-mercaptoethanol to produce a concentration of $5\times10^{-5}$M.

Approximately 24 hours after fusion, the microcultures were supplemented by the addition of HAT media thereto. Thereafter, the hybridoma cell cultures were cloned by limiting dilution using thymocytes and 2-mercaptoethanol.

The hybridoma cell lines are preferably stored in liquid nitrogen. They are cultured in Dulbeco's Modified Eagle Medium with 10% fetal bovine serum, 2 mM L-glutamine, 100 U/ml penicillin, 100 micrograms/ml streptomycin, and $3\times10^{-5}$M 2-mercaptoethanol at 37° C. and 5% $CO_2$.

Alternative methods for cell fusions and cloning can also be used as may presently or hereafter be known in the art.

4. Screening of Monoclonal Antibodies and Hybridomas

The cell fusions resulted in numerous hybridoma cell lines producing various monoclonal antibodies, only some of which bound to the surface of the merozoites. Antibodies in hybridoma supernatants produced 2 distinct patterns of fluorescence on acetone fixed *Babesia bigemina* blood smears. Some reacted with only a portion of the erythrocyte present in a field. By phase microscopy of the same microscope field, it was found that all fluorescent erythrocytes contained parasites. Others reacted only with the parasite, as determined by a pattern of fluorescence compatible with the morphology of *Babesia bigemina* and by comparison of the same field in phase microscopy. Cell lines producing antibodies that reacted only with the fixed parasite were expanded to 24 well plates and screened by IFA of live merozoites. Out of 65 antibodies reacting with fixed parasites, 43 bound to live merozoites. All 43 positive antibodies bound between 70% and 95% of the merozoites in a preparation with a viability of 70%. Reaction of the merozoite preparation with both Ana 13 (monoclonal antibody against normal bovine erythrocytes) and a monoclonal antibody against the parasite surface, produced fluorescence on both the inner parasite membrane and the outer erythrocyte membrane. Supernatants from the initial fusions and from limiting dilution clones produced therefrom were screened to produce the results indicated above by indirect immunofluorescence assay using acetone fixed and live *Babesia bigemina* organisms as described below.

(c) Indirect Immunofluorescence Assay (IFA)—Fixed *Babesia bigemina*

Indirect immunofluorescence of acetone fixed *Babesia bigemina* was performed such as described by T. C. McGuire, G. H. Palmer, W. L. Goff, M. I. Johnson, and W. C. Davis (1984) "Common and Isolate-Restricted Antigens of *Anaplasma marginale* Detected with Monoclonal Antibodies," Infect. Immun. 45:697. Blood smears from *Babesia bigemina* experimentally infected animals were fixed in acetone for 5 minutes and incubated with hybridoma supernatants containing the monoclonal antibodies. In assays involving antibodies raised to immune cattle, bovine serum was incubated with the fixed parasites instead of the monoclonal antibodies. Both were diluted in PBS for 30 minutes at room temperature. The incubated smears were thereafter washed 3 times with PBS. Antibodies which directly bound to the merozoites were detected by binding a labeled second antibody conjugate thereto, such as fluorescein isothiocyanate conjugated to a second antibody (rabbit anti-mouse or rabbit anti-bovine immunoglobulin). Slides were examined on a Zeiss microscope equipped for epffluorescence with a mercury lamp.

(b) Indirect Immunofluorescence Assay (IFA)—Live *Babesia bigemina*

All steps were performed on ice. Gradient separated *Babesia bigemina* merozoites were suspended in PBS containing 0.5% (w/v) bovine serum albumin (hereinafter BSA). Aliquots of $1\times10^7$ FDA positive cells were centrifuged at 2500 G for 5 minutes and resuspended in monoclonal antibody supernatant containing 25 micrograms immunoglobulin or in 100 microliters serum diluted in PBS/BSA. After a 30 minute incubation, the cells were washed 3 times with PBS/BSA by centrifugation at 2500 G. Bound antibodies were detected by incubation for 30 minutes in fluorescein isothiocyanate labeled rabbit anti-mouse or rabbit anti-bovine conjugate followed by washing as described above in the fixed assay. The cell pellet was examined in a wet mount by phase and fluorescence microscopy. Percentage of merozoites bound by monoclonal antibody was calculated by determining the number of fluorescent cells in 500 total cells. Uninfected bovine erythrocyte ghosts were used as control antigen in live IFA.

C. Identification of *Babesia bigemina* Surface Proteins with Exposed Epitopes

Monoclonal antibodies were selected which bound to at least 70% of the parasites in an IFA of live merozoites with viability of 70%. The resulting 43 monoclonal antibodies were further screened by radioimmunoprecipitation of $^{35}$S-methionine metabolically labeled *Babesia bigemina* using procedures as described below.

1. Metabolic Radiolabeling of Parasites

Heparinized blood collected from a splenectomized calf infected with the Mexico stabilate of *Babesia bigemina* was harvested at the time of logarithmic parasite growth. The blood was washed twice in calcium and magnesium from Hank's balanced salt solution (hereinafter HBSS) by centrifugation at 800 G for 10 minutes. The buffy coat and 50% of the packed erythrocyte pellet were removed at each wash. The resulting cell pellet was resuspended to 50% (v/v) with HBSS, and 5 ml aliquots were layered on 40 ml 60%/80% Percoil step gradients prepared by centrifugation at 1000 G for 30 minutes and made isosmotic with HBSS. After centrifugation at 500 G for 30 minutes, the erythrocyte pellet at the bottom of the tube was collected, washed 2 times with HBSS, and resuspended to $2\times10^9$ erythrocytes/ml in ether: Medium-199 without D,L-methionine and sodium bicarbonate (Gibco Laboratories, Chagrin Falls, Ohio); Eagle Minimal Essential Medium modified with Earle's salts without L-glutamine and D,L-methionine (Flow Laboratories, McLean, Va.); or RPMI-1640 Select-Amine Medium without D,L-methionine (Gibco Laboratories, Chagrin Falls, Ohio). Each medium, pH 7.0, also contained 2 mM L-glutamine, 10% (v/v) fetal bovine serum, 100 units/ml penicillin, and 200 micrograms/ml streptomycin. Pooled, uninfected blood from 5 normal calves was processed exactly as infected blood. Total erythrocyte counts, total white blood cell counts, percentage leukocyte contamination, presence and number of reticulocytes (as determined in smears of 0.5% new methylene blue stained cells), and parasitemia were determined on aliquots of the parasitized erythrocytes in media.

A merozoite cell suspension was prepared therefrom using $^{35}$S-methionine at a concentration of 100 microCi/3×10$^9$ erythrocytes, and was cultured in a candle jar using a procedure such as described by P. Timms (1980) "Short Term Cultivation of Babesia Species," Res. Vet. Sci. 29:102. Cultures were incubated for 3-9 hours, washed 5 times with HBSS, lysed in buffer containing 50 mM Tris (tromethamine), 5 mM ethylenediaminetetraacetic acid (EDTA), 5 mM iodoacetamide, 1 mM phenylmethylsulfonylfluoride, 0.1 mM N-alpha-rho-tosyl-L-lysyl chloromethyl ketone, and 1% (v/v) Nonidet P-40 (lysis buffer), and frozen at −70° C. until use. Trichloroacetic acid precipitable radioactive counts of the resulting radiolabeled parasites were determined by filter paper techniques.

Alternatively, parasite proteins were radiolabeled with $^{35}$S-methionine in short term culture, or by incorporation of $^{35}$S-methionine, $^3$H-amino acids, $^3$-H-glucosamine, or $^3$H-myristic acid into parasites grown in continuous culture. For metabolic radiolabeling, parasites grown in 24 well plates were fed with 1.0 ml of complete medium 24 hours after a routine split. One to four hours later, 1.0 ml of culture medium overlying the infected erythrocytes was replaced with 200-400 μCi of lyophilized $^{35}$S-methionine (>800 Ci/mmole in 20 mM potassium acetate containing 0.1% 2-mercaptoethanol, Amersham, Arlington Heights, Ill.), $^3$H-L-amino acid mixture (in 0.1N hydrochloric acid, Dupont, Wilmington, Del.), $^3$H-glucosamine hydrochloride (30-60 Ci/mmole in aqueous buffer, Dupont), or $^3$H-myristic acid (10-60 Ci/mmole in ethanol, Dupont) resuspended in 1.0 ml methionine deficient medium ($^{35}$S-methionine) Or complete medium ($^3$H-amino acids, $^3$H-glucosamine, and $^3$H-myristic acid). Radiolabeled parasites were harvested 16-18 hours later, washed, and lysed in 1% (v/v) Nonidet P-40 (LKB, Bromma, Sweden).

2. Iodination of Erythrocyte Ghosts

Washed normal bovine erythrocytes pooled from 5 calves were lysed and labeled with Na$^{125}$I by lactoperoxidase catalyzed iodination such as described by G. H. Palmer and T. C. McGuire (1984) "Immune Serum Against *Anaplasma marginale* Initial Bodies Neutralizes Infectivity for Cattle," J. Immunol. 133:1010, which is hereby incorporated by reference. The procedure was slightly modified by separation of labeled cells from free iodine prior to dialysis through a 4 ml Dowex 1-X8-200 column (Bio-Rad Laboratories, Richmond, Calif.) equilibrated in PBS. Dialyzed samples were mixed with twice their volume of lysis buffer and frozen at −70° C. until use.

3. Radioimmunoprecipitation

Immunoprecipitation of radiolabeled antigen was performed as is known in the art, such as described by G. H. Palmer and T. C. McGuire (1984) J. Immunol., supra. Radiolabeled antigert was centrifuged at 135,000 G for 9 hours, passed through a 0.45 micron filter, and sonicated 4 times at 75 watts for 15 seconds each. One million to 2 million TCA precipitable counts were incubated with 5 micrograms of monoclonal antibody or 5 microliters bovine immune serum for 30 minutes. Immune complexes were precipitated by the addition of second antibody (rabbit anti-murine immunoglobulin or anti-bovine IgG$_1$ and IgG$_2$) and 10% (v/v) protein A bearing *Staphylococcus aureus* (Calbiochem-Behring Corp., La Jolla, Calif.). Washing and elution of bound antigert was performed as also described by G. H. Palmer and T. C. McGuire (1984) J. Immunol., *supra*.

For electrophoresis of unreduced proteins, precipitated antigen was boiled in sample buffer without beta-mercaptoethanol. Prior to application of the unreduced sample to a sodium dodecyl surfate polyacrylamide gel electrophoresis (hereinafter SDS-PAGE) gel, 1.5 mM iodoacetate was added at a ratio of 1 part iodoacetate to 10 parts antigen in sample buffer such as described by A. Johnstone and R. Thorpe (1982) "Polyacrylamide Gel Techniques," In *Immunochemistry in Practice*, Blackwell Scientific Publications, Boston, p. 141. Samples were either frozen at −70° C. until used or loaded directly onto SDS-PAGE gels.

4. Sodium Dodecyl Sulfate Polyacrylamide Gel Electrophoresis (SDS-PAGE).

Metabolically radiolabeled parasitic antigen or immunoprecipitates were mixed with 3 times volume of SDS-PAGE sample buffer to a final concentration of 25 mM Tris, pH 6.8, 2% (w/v) sodium dodecyl sulfate, 15% (v/v) glycerol, 2.5% beta-mercaptoethanol, and a few crystals of bromophenol blue. They were boiled for 3 minutes and electrophoresed in a 7.5% to 17.5% SDS-PAGE gradient slab gel with a 5% stacking gel such as described by B. Takacs (1979) "Electrophoresis of Proteins in Polyacrylamide Gels," In *Immunological Methods*, edited by T. Lefkovitz and B. Persin, Academic Press, New York, p. 81. The SDS-PAGE gels were processed for autoradiography. For immunoblotting,, 1×10$^8$ gradient separated merozoites were electrophoresed in 7.5%-17.5% gradient SDS-PAGE and transferred to nitrocellulose. Immunoblots using bovine antibodies detected with $^{125}$I-labeled protein G or rabbit antibodies detected with $^{125}$I-labeled protein A were performed as described in the literature (McElwain et al. [1987] supra; Hines, S. A., T. F. McElwain, G. M. Buening, G. H. Palmer [1989] Mol. Biochem. Parasitol. 37:1-10). $^{14}$C-labeled proteins used for molecular weight comparisons (Amersham, Arlington Heights, Ill.) consisted of myosin, 200,000 m.w.; phosphorylase b, 92,500; bovine serum albumin, 69,000; ovalbumin, 46,000; carbonic anhydrase, 30,000; and lysozyme, 14,300. For visualization of unlabeled proteins in SDS-PAGE, gels were stained with either 0.075% Coomassie blue or silver nitrate as described by B. Takacs (1979), *supra*; and J. H. Morrissey (1981) "Silver Stain in Proteins in Polyacrylamide Gels: A Modified Procedure with Enhanced Uniform Sensitivity," *Anal. Biochem.* 117:307, respectively. Molecular weight standards used in Coomassie blue and silver stained gels (Pharmacia Inc., Piscataway, N.J.) consisted of phosphorylase b, 94,000 m.w.; bovine serum albumin, 67,000; ovalbumin, 43,000; carbonic anhydrase, 30,000; soybean trypsin inhibitor, 20,100; and alpha-lactalbumin, 14,400. Alternative electrophoretic or other analyses may also be used for establishing molecular weights.

Nineteen of the 43 IFA surface reactive monoclonal antibodies immunoprecipitated a protein labeled with $^{35}$S-methionine. Five hybridoma cell lines identified as 14.1, 14.16, 14.20, 14.29, and 14.52 were selected for further study and were cloned by limiting dilution. These cell lines produced monoclonal antibodies that precipitated major surface proteins with relative molecular weights in SDS-PAGE of 72 kDa, 58 kDa, 55 kDa, 45 kDa, and a group of three proteins at 36 kDa, 20 kDa, and 16 kDa. None of the monoclonal antibodies immunoprecipitated a Na$^{125}$I labeled normal bovine erythrocyte protein. Table I summarizes the specificities of these 5 monoclonal antibodies in immunoprecipitation.

TABLE I

Surface reactive monoclonal antibodies against *Babesia bigemina*

| Monoclonal Antibody | Isotype | Protein Group | Protein Specificity[a] Major[b] | Additional[c] |
|---|---|---|---|---|
| 14.1 | IgG$_{2a}$ | Bp45 | 45 kDa | 49, 36 kDa |
| 14.20 | IgG$_1$ | Bp55 | 55 kDa | 43 kDa |
| 14.29 | IgG$_1$ | Bp72 | 72 kDa | — |
| 14.16 | IgG$_1$ | Bp58 | 58 kDa | 36, 35, 33 kDa |
| 14.52 | IgG$_1$ | Bp36 | 36, 20, 16 kDa | — |

[a] as determined by immunoprecipitation of $^{35}$S-methionine labeled *Babesia bigemina*
[b] immunoprecipitated from all antigen preparations
[c] immunoprecipitated from some antigen preparations Monoclonal antibody 14.52 consistently immunoprecipitated multiple proteins. Three surface reactive monoclonal antibodies 14.1, 14.16, and 14.20—each immunoprecipitated additional $^{35}$S-methionine labeled proteins when antigens from different labelings were used under the same labeling conditions. The molecular weights of these precipitated proteins are as follows: monoclonal antibody 14.1–49 kDa and 36 kDa; monoclonal antibody 14.16–36 kDa, 35 kDa, and 33 kDa; and monoclonal antibody 14.20–43 kDa. In addition, the relative mobility of the major protein precipitated from the merozoite antigens by monoclonal antibody 14.20 varied from 58 kDa to 55 kDa. Under non-reducing conditions, all immunoprecipitated proteins migrated identically to those electrophoresed under reducing conditions.

Two of the antibodies that immunoprecipitated more than one radiolabeled antigen, 14.1 and 14.16, bound to gradient separated merozoite proteins transferred to nitrocellulose. Monoclonal antibody 14.1 recognized only one band with a relative mobility of 45 kDa, while monoclonal antibody 14.16 recognized immunoprecipitated proteins 58, 36, 35, and 33 kDa, as well as proteins at 47 and 43 kDa that were not precipitated. The two additional monoclonal antibodies that immunoprecipitated multiple proteins, 14.20 and 14.52, failed to react with merozoite proteins on nitrocellulose.

D. Identification of Proteins Recognized by Bovine Immune Sera

Immune bovine serum obtained from a calf experimentally infected with the Mexico isolate of *Babesia bigemina* was used to immunoprecipitate $^{35}$S-methionine labeled proteins from the Mexico isolate. Serum from day 25 post-inoculation (immediately following complete recovery of the calf from acute clinical babesiosis) immunoprecipitated approximately 40 radiolabeled proteins. These included proteins having approximate molecular weights of 72 kDa, 58 kDa, 55 kDa, 45 kDa, and 36 kDa. Using the same radiolabeled antigen (Mexico isolate), immune bovine serum obtained from a calf experimentally infected with the Kenya isolate of *Babesia bigemina* immunoprecipitated 5 proteins that electrophoresed with relative mobilities identical to those recognized by immune serum against the Mexico isolate. When bovine immune serum and monoclonal antibody precipitates were electrophoresed in adjacent SDS-PAGE lanes, the proteins containing surface exposed epitopes recognized by monoclonal antibodies co-migrated with major proteins recognized by bovine immune serum.

Five major $^{35}$S-methionine proteins migrating at molecular weights of 72, 58, 55, 45, and 36 kDa in SDS-PAGE are immunoprecipitated by monoclonal antibodies surface reactive to the merozoites of *B. bigemina*. The inability of these same monoclonal antibodies to immunoprecipitate iodinated normal erythrocyte proteins, the absence of radiolabel incorporation in normal erythrocyte cultures, and the relative lack of cells (reticulocytes, leukocytes, and platelets), other than parasites, capable of methionine incorporation in *Babesia bigemina* cultures indicates that the surface proteins are of babesial origin.

In the absence of beta-mercaptoethanol and the presence of iodoacetate, *Babesia bigemina* surface proteins migrate exactly as they do in the presence of beta-mercaptoethanol, demonstrating that they are not disulfide-bonded subunits of multimerle proteins. By western blotting, monoclonal antibody 14.1 binds only to a 45 kDa protein, indicating that the additional proteins co-precipitated by this antibody are part of a membrane complex not disrupted by NP-40 detergent. However, as demonstrated in western blots, all proteins immunoprecipitated by monoclonal antibody 14.16 contain the epitope to which this antibody binds and thus are specifically precipitated by it.

The antigenic surface proteins gp36, gp45, gp55, gp55, p58, and p72 are protease sensitive. As such they can easily be mimicked by synthetic peptides or polypeptides expressed in a foreign bacterium, yeast, or virus containing the gene coding for the epitopes. Availability of the corresponding monoclonal antibodies as shown in Table I above makes synthetic peptide and gene cloning procedures practical alternatives for production of vaccines according to this invention.

E. Construction and immunoscreening of cDNA expression library from *B. bigemina*

For the construction of a cDNA construction library from *B. bigemina*, the Mexico isolate was cloned by limiting dilution in 96 well plates. The isolate clone, JG-29, was derived from the second cloning and, assuming a Poisson distribution of parasites within wells in each cloning set, has a probability of p=0.98 of single infected cell derivation.

Biologically cloned Mexico strain JG-29 infected erythrocytes were concentrated from culture. Poly A(+) RNA was purified from concentrated infected erythrocytes by the method of Bradley et al. (Bradley, J. E., G. A. Bishop, T. St. John, and J. A. Frelinger [1988] Biotechniques 6:114-116) and used as template for cDNA synthesis by a modified Gubler and Hoffman technique (Pharmacia PL Biochemicals, New Jersey, USA). The cDNA was ligated to lambda Zap II phage expression vector and packaged using Gigapack gold packaging system (Stratagene Inc., La Jolla, Calif.) according to the manufacturer's instructions. The cDNA library was screened by modification of the method of Young and Davis (Young, R. A., R. W. Davis [1983] Science 222:778-782) using XL-1 Blue host cells and NZY medium. Plaque lifts on nitrocellulose filters were washed three times with TNTP (10 mM Tris-HCl pH 7.6, 150 mM NaCl, 0.05% Tween-20 and 1 mM PMSF), and blocked overnight at 4° C. in blocking buffer (TNTP containing 5% non-fat dry milk). Filters were transferred to a solution containing a 1:500 dilution of monospecific rabbit antiserum (R931) against native p58 that had been preadsorbed with *E. coli* lambda phage lysate and incubated for 1 hour at room temperature. Alternatively, filters were incubated with 1 μg ml$^{-1}$ monoclonal antibody 14/16.1.7 recognizing native p58, followed by rabbit anti-murine immunoglobulin second antibody. The filters were washed three times with blocking buffer, incubated for one hour with 5×10⁶ cpm of $^{125}$I-Protein A (Amersham, Arlington Heights, Ill.), and washed 3 additional times with TNTP (the second containing 0.01% v/v Triton X-100) before air drying and autoradiography. All antibodies and $^{125}$I-Protein A were diluted in blocking buffer. Positive plaques were eluted in buffer containing 0.05M Tris, 0.1M NaCl, 0.008 M MgSO₄, and 2% w/v gelatin and rescreened until 100% plaque purification was achieved.

F. Isolation, nucleic acid sequencing, and differential expression of the p58 gene family of *Babesia bigemina*

1. Isolation of genomic DNA and PCR amplification of p58 gene copies. *B. bigimena* DNA was amplified using 2/μm each of ES55 and ES57 primers (see Table II) corresponding to the 5' and 3' ends of the p58 gene sequence shown in SEQ. ID 1. DNA amplifications were performed according to the manufacturer's conditions. The p58 genes containing 5' and 3' flanking sequences were amplified using 35 cycles of denaturation (92° C., 1 minute), annealing (55° C. 3 minutes), and polymerization (72° C., 3 minutes). The amplified product was run on 1% agarose gel to confirm the successful amplification of predicted size (about 2000 base pairs) DNA fragment. Southern analyses of EcoRI and PstI digested genomic DNA from JG-29, a biologically cloned strain of *B. bigemina*, and the source of the molecularly-cloned gene, demonstrate the presence of multiple fragments that hybridized with a probe made from the cDNA clone. Since the cDNA sequence does not contain any PstI site, and only a single EcoRI site, the size of the fragments and presence of more than one band when cut with EcoRI and more than two bands when cut with PstI shows that additional gene copies having divergent sequences were present within the parasite genome.

TABLE II

Oligonucleotide primers used to identify p58 multiple gene family

| Oligonucleotide | Size (bases) | Gene copy[1] | Nucleotide position |
|---|---|---|---|
| ES53 | 21 | Bbg 7, 14, 9, 13 | 182–202 |
| ES55 | 20 | Bbg 7, 14, 9, 13 | 1–20 |
| ES57 | 20 | Bbg 14, 13 | 1943–1962 (RC)[3] |
| ES57 | 20 | Bbg 7, 9 | 1986–2005 (RC) |
| ES59 | 21 | Bbg 14, 9 | 375–395 (RC) |
| ES61 | 21 | Bbg 7, 13 | 375–395 (RC) |
| ES104 | 30 | Bbg 7, 9 | 1629–1658 (RC) |
| ES105 | 30 | Bbg 14, 13 | 1515–1544 (RC) |

[1]Denotes the p58 gene copy to which this oligonucleotide primer will hybridize.
[2]Denotes the nucleotide position of the oligonucleotide primer based on the reported p58 gene sequence.
[3]RC infers that this oligonucleotide primer corresponds to the DNA sequence on the noncoding DNA strand.

2. Molecular cloning and sequence analysis of PCR amplified product.

PCR amplified DNA was treated with Klenow DNA polymerase for 1 hour at 22° C. to generate blunt end molecules. The blunt-ended DNA was isolated by standard agarose gel electrophoresis and electroelution techniques. The isolated DNA was ligated into the SmaI site of pGEM3Zf(−) using 1 unit of T4 DNA ligase at 16° C. The ligated DNA was used to transform competent JM109 cells. Recombinants were selected by plating on TYN agar plates containing 0.12 mg/ml X-Gal and 100/μg/ml ampicillin. Several recombinants (white colonies) were picked for miniprep DNA analysis, and transformants carrying an insert of approximately 2 kb were grown as batch cultures and the plasmid DNA purified by CsCl gradient centrifugation. Restriction digestion and agarose gel electrophoresis of these recombinants categorized them into four groups based on the presence or absence of EcoRI and/or PstI site(s). Plasmids containing the p58 gene from each representative group (pBbg7, pBbg9, pBbg13, and pBbg14) were isolated and subjected to DNA sequence analysis (FIG. 2). Recombinant pBbg13 (1962 bp, single EcoRI and PstI sites at positions 1080 and 1869, respectively) was identical to the cDNA sequence described herein except for a single nucleotide substitution (G at position 1029 instead of A). However, as depicted schematically in FIG. 3, recombinant clones pBbg7 (2005 bp, no EcoRI and single PstI site at position 1912) and pBbg14 (1962 bp, single EcoRI and two PstI sites at positions 1080, and 423 and 1869, respectively) contained a region of sequence diversity when compared to Bbg13 that was localized toward the 3' and the 5' ends, respectively. In addition, recombinant clone pBbg9 (2005 bp, no EcoRI but two PstI sites at positions 423 and 1912) incorporated both the regions of sequence variation. A third PstI site has been found to be located 48 bp upstream of the 5' end of the amplified sequence in a partially sequenced genomic clone. Thus, based on the size of the PCR amplified products, two short (Bbg13 and Bbg14, 1962 bp) and two long (Bbg7 and Bbg9, 2005 bp) copies of the p58 gene (including the 5' and 3' non-coding regions) were identified. However, in spite of the variation in the length of the PCR amplified products, several features were conserved amongst all four gene copies. These were:

(i) the position of the initiation of translation of the ORF (nucleotide bases 186–188); and (ii) the conservation of the nucleotide sequence at the extreme 5' and 3' ends of the ORF as well as in the central portion of the gene. Despite the variation of sequence which frequently resulted in amino acids changes, the number of nucleotides in the p58 ORF of Bbg14 was identical to Bbg13 and the original cDNA clone sequenced. However, the divergent sequence at the 3' end in Bbg7 and Bbg9 introduced a stop codon after position 1511, shortening the ORF from 1440 to 1326 bases. Therefore, longer PCR amplified products actually had a shorter p58 ORF. Alignment of the four sequences was performed using the "Clustal" program of Higgins and Clark, supra, which is known in the art. Alignment revealed that, apart from significant changes in the gene sequence, sporadic single base substitutions were also present, scattered throughout the sequence in Bbg7, Bbg9, and Bbg14. An unamplified genomic library of *B. bigemina* was screened for the presence of all four p58 gene copies. Lambda Gem11 clones were isolated containing each of the four p58 gene copies as identified on the basis of restriction mapping data, thus confirming that the amplification of four p58 gene copies was not an artifact of the PCR amplification procedure. The predicted amino acid sequence encoded by these four gene copies reflected the changes seen in the nucleotide sequences (FIG. 4). When compared to the copy representing the cDNA (Bbg13), many substitutions in amino acids were either perfectly matched or well matched. The sporadic nucleotide substitutions, though very few in number, mainly resulted in nonconservative change in the amino acids. Overall, the number of amino acids in the predicted protein sequence was 480 for Bbg13 and Bbg14 and 442 for Bbg7 and Bbg9.

3. RNA-PCR analyses. To determine if one or more copies of the p58 gene were expressed, RNA blotting experiments were carried out using cDNA and clone-specific oligonucleotide probes. The location of each clone-specific primer is depicted in Table II.

Total RNA was isolated by the method of Chomczynski and Sacchi (Chomczynski, P., N. Sacchi [1987] Analyt. Blochem. 162:156-159) from 99% parasite-infected RBC, purified on percoll gradient. Amplification of RNA sequences using PCR involved: (a) DNase treatment, (b) cDNA synthesis, and (c) PCR with appropriate oligmers. Total RNA (8 $\mu$g) was digested with 17 units of RNase free DNase in the presence of 20 units of RNasin and 2 mM $MgCl_2$ in a total volume of 20 $\mu$l for 1 hour at 37° C. After 1 hours, DNase was inactivated by heating to 95° C.; or 5 minutes and the sample snap-cooled on ice. Five $\mu$l aliquots were transferred to four microfuge tubes and cDNA synthesis reaction carried out at 43° C. for 1 hour in a total volume of 20 $\mu$l 1× PCR buffer containing 1 mM each of the four dNTPs, 20 units RNasin, and 1 $\mu$M of either ES104 or ES105 (downstream primers) and in the presence or absence of 200 units of Moloney murine leukemia virus (M-MLV) reverse transcriptase. Treatment with DNase and a negative control lacking reverse transcriptase in the experimental design was included to eliminate the possibility of detecting any spurious DNA amplification that could be attributed to trace amounts of parasite DNA. Following cDNA synthesis, the reverse transcriptase was inactivated by heating to 95° C. for 5 minutes and the sample snap-cooled on ice. Second strand synthesis and amplification was performed in a 100 $\mu$l reaction containing 1× PCR buffer, 1 $\mu$M ES53 and ES104 or ES105, 5 units Taq polymerase, and the entire cDNA reaction (20 $\mu$l). In separate reactions (positive controls), 1.5 $\mu$g of Bbg14 and 2.25 $\mu$g. of Bbg9 DNA were also amplified simultaneously. The conditions for amplification were identical to those described above, and a 5 $\mu$l sample of each PCR reaction was analyzed on 1% agarose gel.

4. Northern and southern blot analyses. Formaldehyde-denatured total RNA (21 $\mu$g) was fractionated on 1.2% formaldehyde-agarose gel, transferred to nitrocellulose membrane, and hybridized with $^{32}$P-labeled probe derived from the p58 cDNA gene using the random primer DNA synthesis method in the presence 6. In vitro translation studies. Since the data from DNA sequence and hybridization analyses suggested that two different size transcripts were present in the merozoite, poly A+mRNA was isolated and translated in vitro using a rabbit reticulocyte lysate system as per supplier's instructions (Amersham Corporation, USA). The in vitro translated products were then immunoprecipitated with a polyclonal antibody directed against p58 and subjected to SDS-PAGE. Two protein species having apparent $M_r$ values of 58,000 and 55,000 were detected. The relative amounts of the protein species immunoprecipitated were consistent with relative abundance of the longer and shorter transcripts observed by northern blot analyses. These results are similar to that observed when blood stage parasites are metabolically labeled in culture with $^{35}$S-methionine, and the p58 proteins immunoprecipitated with the same rabbit polyclonal antibody.

G. Excision of phagemid and detection of recombinant protein by immunoblotting

Phagemid was excised according to manufacturer's instructions (Stratagene Inc., La Jolla, Calif.). XL-1 Blue E. coli containing rescued phagemid were plated on Luria-Bertani agar medium containing 100 $\mu$g ml$^{-1}$ ampicillin. Colonies were picked and tested for the expression of recombinant p58 as above after replica plating and colony lifts onto nitrocellulose. Positive colonies from the master plate were grown in 50 ml Luria-Bertani medium with 100 $\mu$g ml$^{-1}$ ampicillin for 9 hours at 37° C. Bacteria were washed once with 0.01M sodium phosphate, 0.15 M NaCl, pH 7.2 and suspended in 5 ml of the same buffer. One hundred $\mu$l of this suspension were mixed with an equal volume of 2× lysis buffer (100 mM Tris HCl pH 8.0, 10 mM EDTA, 2% NP-40, 2 mM PMSF and 0.2 mM TLCK) and 100 $\mu$l of 3× sodium dodecyl sulfate polyacrylamide gel (SDS-PAGE) sample reducing buffer, boiled for 3 minutes, and electrophoresed through a 7.5%-17.5% SDS-gradient polyacrylamide gel system. The separated proteins were transferred to a nitrocellulose filter and processed as above for immunoscreening. of $^{32}$P-dCTP. Prehybridization and hybridization were carried out as described previously (Maniatis, T., E. F. Fritsch, J. Sambrook [1982] *Molecular cloning: a laboratory manual*, Cold Spring Harbor Laboratory, Cold Spring Harbor, N.Y.) at 68° C. for 4 and 15 hours, respectively. Filters were washed once with 1× SSC containing 0.1% SDS at room temperature for 20 minutes, followed by two 20 minute washes with 0.2× SSC containing 0.1% SDS at 65° C. Bands hybridizing to the probe were detected by standard autoradiographic technique. Northern analysis utilizing a p58 cDNA probe identified a dominant RNA species of 1.9 kb and an RNA species hybridizing less intensely at 1.65 kb. No hybridization was evident when bovine WBC RNA was run as a positive control.

For southern analysis, either restriction digested *B. bigemina* genomic DNA or 5 $\mu$l of each RNA-PCR reaction was run on a 1% agarose gel and the DNA transferred to nitrocellulose membrane as described. The membrane was processed and probed exactly as for northern blotting.

5. Slot blotting with specific oligonucleotides. To further resolve the expression of p58 gene copies, oligonucleotides specific for the original cDNA clone and Bbg13 or variant gene sequences (Bbg7, 9, 14) were synthesized and used in slot blotting experiments. Initially, a RNA-PCR amplification produced predicted size fragments using a conserved upstream primer and the variant downstream primers. The downstream primer ES104 amplified DNA was several-fold greater than the DNA amplified by the downstream primer ES105. To ascertain if all four copies were represented in those two bands, RNA-PCR products were slot blotted and oligonucleotide-specific hybridization performed. Oligonucleotide probes derived from ES59, ES104, and ES105 hybridized as was expected, but the ES61 probe failed to hybridize with ES105 amplified DNA. The results indicate that the mRNA transcribed from gene copies Bbg9, Bbg13, and Bbg14 were present in the blood stages but that mRNA from the Bbg7 gene copy was not present or was in such low abundance that it was not detectable by the methods employed in this study.

H. Preparation of antiserum to recombinant p58 protein

XL-1 Blue cells expressing recombinant p58 were freeze-thawed and sonicated on ice five times for 15 seconds each. New Zealand white rabbits were immunized four times at weeks 0, 1, 2, and 4 by intraperitoneal inoculation with $5 \times 10^5$ sonicated bacterial cells emulsified in complete (first immunization) or incomplete (3 booster immunizations) Freund's adjuvant. Serum was harvested at week 7 and used in immunoprecipitation studies. The JG-29 strain of *B. bigemina* was metabolically labeled with $^{35}$S-methionine and immunoprecipitated with rabbit serum or monoclonal antibody as previously described [4, 5]. The samples were analyzed by either 10% or 7.5%–17.5% gradient SDS-PAGE, and the bands visualized using standard fluorographic techniques.

I. DNA and mRNA Sequencing

Plasmid pBbg58 was purified by CsCl centrifugation. DNA was sequenced by dideoxy chain termination method using M13 reverse and universal primers, several synthetic oligonucleotides (16 to 20-mers) and Sequenase DNA sequencing kit, version 1.0/2.0 from United States Biochemical Corporation, Ohio, U.S.A. Both strands were sequenced and the data analyzed by PCGene computer software. To obtain the complete sequence of the gene encoding p58, a genomic library of the Mexico isolate of *B. bigemina* was constructed. Genomic DNA was partially digested with Sau3A and size fractioned on a 10–40% continuous sucrose gradient. Fragments ranging from 9–23 kb were isolated, ligated to BamHI digested lambda GEM-11 genomic cloning vector (Promega Corp., Wis., USA) and packaged using Gigapack gold packaging extracts (Stratagene Inc., La Jolla, Calif.). The genomic library was screened for positive plaques using a $^{32}$P-labeled probe (see below-Southern blotting) derived from the cDNA insert of pBbg58. Ten positive clones were picked and plaque purified. The DNA from one recombinant, designated clone 3.2, was sequenced with appropriate primers to obtain the complete p58 gene sequence. Messenger RNA was isolated as above and sequenced. The primer was the reverse complement of bases 256 through 275 of the DNA sequence.

J. Southern blotting

*B. bigemina* genomic DNA isolated from infected erythrocytes was digested with restriction endonucleases. The fragments were separated by agarose gel electrophoresis and transferred to nitrocellulose. Blots were hybridized using a $^{32}$P-labeled p58 cDNA probe prepared by random prime labeling at 65° C. for 16 hrs ($6 \times$ SSC, $5 \times$ Denhardts solution, 0.1% SDS and 100 μg sonicated salmon sperm DNA). Filters were washed two times in $2 \times$ SSC containing 0.1% SDS for 5 minutes and then four times with $0.2 \times$ SSC at 52° C. for 30 minutes. A Hind III digest of bacteriophage lambda was used as a molecular weight standard on agarose gels.

K. Preparation of Vaccine and Immunization of Cattle with Purified Antigenic Surface Proteins of the Merozoite Stage of *Babesia bigemina*

1. Vaccine Preparation. Mexico isolate of *Babesia bigemina* cryopreserved as described above was utilized in preparation of a vaccine. Gradient polyacrylamide gel techniques, SDS-PAGE sample buffer, and autoradiography techniques were also utilized as described above.

Monoclonal antibodies 14.1, 14.16, 14.20, and 14.52 that recognize *Babesia bigemina* merozoite surface proteins were prepared as described above. Monoclonal antibody 14.72 was lost in dilution cloning. Ascitic fluid was generated by intraperitoneal inoculation of pristane primed BALB/c mice with a $5 \times 10^6$ twice cloned hybridoma cells for each of the four remaining monoclonal antibodies. Purification of monoclonal antibodies from such ascitic fluid was performed by diethylaminoethyl cellulose chromatography (DE-52, Whatman Ltd., Maidstone Kent, England) of 50% ammonium sulfate precipitated immunoglobulin (from ascitic fluid) in 0.032 M Tris, pH 7.4. Columns were eluted by 0,032 M Tris, pH 7.4, followed by a gradient of 0 to 0.2M NaCl in the same buffer. Protein content of 5 ml fractions from the columns was monitored by $OD_{280}$. Purity of the isolated monoclonal antibodies was further established in Coomassie blue stained gradient polyacrylamide gels (as above) loaded in each lane with 50 micrograms of protein from column fractions. Other suitable procedures for purification and purity assurance can alternatively be used.

These purified monoclonal antibodies in 0.1M NaHCO$_3$, 0.5M NaCl, pH 8.3 were rotated at room temperature for 2 hours with cyanogen bromide (CNBr)-activated Sepharose 4B beads (Pharmacia Fine Chemicals, Uppsala, Sweden) that had been washed with 0.001 N HCl. Antibodies were added at a ratio of 10 mg protein to 1 ml swollen beads. Non-specific binding sites were blocked by rotating coupled beads for 2 hours at room temperature in 0.2M glycine, pH 8.0. They were then washed 3 times each with alternating buffers of 0.1M. sodium acetate, 1.0M NaCl, pH 4.0; and 0.1M NaHCO$_3$, 0.5M NaCl, pH 8.3; and stored at 4° C. in buffer containing 50 mM Tris, 5 mM EDTA, 5 mM iodoacetamide, 1 mM phenylmethylsulfonylfluoride (hereinafter PMSF), and 0.1 mM N-alpha-rho-tosyl-L-lysyl chloromethyl ketone.

Immunoaffinity chromatography techniques were then performed using the purified monoclonal antibodies on the Sepharose bead matrices for each of the four monoclonal antibodies. Specifically, whole blood collected from splenectomized calves experimentally infected with the Mexico isolate of *Babesia bigemina* was collected at peak parasitemia, washed three times with PBS to remove leukocytes, and stored at −70° C. as a blood stabilate containing packed erythrocytes 1:1 (v/v) with a cryopreservant at 10% (w/v) polyvinylpyrrolidone and 2% (w/v) glucose (crude antigen). This crude antigen was thawed at 37° C., diluted with cold PBS containing 1.0 mM PMSF, and washed three times with the same buffer at 22,000 G. The cell pellet was solubilized in buffer containing 50 mM Tris, 5 mM EDTA, 5 mM iodoacetamide, 1 mM PMSF, 0.1 mM N-alpha-rho-tosyl-L-lysyl chloromethyl ketone, and 1% (v/v) Nonidet P-40 (lysis buffer) on ice for 1 hour. Crude solubilized antigen was centrifuged for 1 hour at 135,000 G, filtered through a 0.45 micron membrane, and sonicated two times at 100 watts, 1 minute each, on ice with a Braun-sonic 1510 ultrasonicator (Braun Instruments, San Francisco, Calif.).

The solubilized antigens prepared from the infected blood were passed twice through the four monoclonal antibody-coupled Sepharose 4B columns hooked in series (750 microliters of packed wet beads each) at a flow rate of 25 ml/hour. The columns were washed sequentially with a solution containing 0.2M Tris, 0.005M EDTA, 0.1M NaCl, 0.015M NaN$_3$, pH 7.6 (hereinafter TEN) containing 1% (v/v) NP-40 and 0.1 mM PMSF; and TEN with 0.1 mM PMSF but without NP-40 detergent. They were then pre-eluted individually with 10 ml of 0.1 M glycine-NaOH, 1M NaCl, 0.5% (w/v) deoxycholate, pH 10.0. Bound merozoite proteins were eluted from individual columns with 5 ml of 0.05M diethylamine, 0.5% (w/v) deoxycholate, pH 11.5 directly into siliconized test tubes containing 0.5 ml of 1M Tris, pH 8.5; and dialyzed against PBS to remove diethylamine and detergent. The amount of protein in the dialyzed elutes were assayed. Purity of the eluted proteins was established in silver stained polyacrylamide gels loaded with 5 micrograms protein/lane. $^{35}$S-methionine biosynthetically labeled *Babesia bigemina* proteins were also purified by immunoaffinity chromatography exactly as above.

2. Immunization of Rabbits with Purified Surface Proteins

Individual rabbits were immunized subcutaneously with 25 μg of one of the four purified surface proteins in Freund's complete adjuvant. Three booster immunizations of 15 μg each in Freund's incomplete adjuvant were given at 1–2 week intervals, and serum was harvested one week later. All sera were tested by ELISA against the respective immunogen and had endpoint titers of 10$^4$. Specificity of the antibody response was confirmed by immunoprecipitation and immunoblot as above.

3. Immunization of Cattle

Four different immunogenic agents containing surface proteins of *Babesia bigemina* protein groups (protein groups p58, gp55, gp45, and gp36) were purified by monoclonal antibody immunoaffinity chromatography as described above. Twenty-five 3 month old Holstein calves were randomly assigned to 5 groups of 5 calves each. Each group was immunized intramuscularly with one of the four purified protein groups or with ovalbumin, 50 micrograms/calf, in 1 ml Freund's complete adjuvant, followed by intramuscular immunizations with 50 micrograms of the same protein in 1 ml of Freund's incomplete adjuvant at 2 week intervals until 5 total immunizations had been administered. One week following the last immunization, all calves were challenged by intravenous inoculation of freshly collected, heparinized whole blood containing 3×10$^9$ blood stage *B. bigemina* from a splenectomized calf experimentally infected with the Mexico isolate. Experimental animals were monitored by daily determination of rectal temperature, packed cell volume (PCV), parasitemia (as determined by calculating the percentage of 1000 erythrocytes containing parasites in a modified Wright's stained blood smear), and the presence or absence of hemoglobinuria. All calves immunized with a merozoite surface protein responded by production of antibodies thereto as shown by the ELISA described below.

Samples of immunized calf blood were also analyzed by immunoprecipitation of $^{35}$S-methionine labeled parasites as described hereinabove. $^{35}$S-methionine biosynthetically labeled *Babesia bigemina* was prepared, and immunoprecipitation of radioactive antigen were performed as described above. The immune sera identified the major proteins present in the vaccines prepared as described. Additional proteins present in the p58 antigen (36, 35, and 33 kD) and the gp36 antigert (20 and 16 kD) were also recognized by the sera from calves immunized with those antigens. A 72 kD protein not seen in immunoprecipitation or affinity purification using monoclonal antibody 14.20 was precipitated by sera from calves immunized with gp55. Sera from ovalbumin immunized calves did not precipitate a radiolabeled protein.

Calves immunized with gp45, gp55, and p58 experienced significantly reduced peak parasitemia after challenge when compared to ovalbumin inoculated calves. Calves immunized with purified merozoite proteins gp45, gp55, and gp36 experienced less temperature increase associated with babesiosis when compared to the ovalbumin inoculated control group. There was also some indication that immunization using gp45, gp55, and p58 may reduce erythrocyte loss experienced by the challenged calves. Additionally, 4 of 5 ovalbumin inoculated calves experienced hemoglobinuria, whereas only 1 of 5 gp55 and 0 of 5 gp45 immunized calves had detectable hemoglobinuria after challenge.

The serum antibody titer of each calf was measured by ELISA and IFA of live merozoites and is presented in Table III. As shown, the ELISA titer of most calves reached 10$^4$. Two gp45 and two p58 immunized calves had titers of 5×10$^5$, while one gp36 and one gp55 immunized calf attained only a 10$^3$ titer. Sera from all calves immunized with a *B. bigemina* surface protein bound to live gradient separated merozoites in IFA. None of the proteins induced an antibody titer against surface exposed epitopes greater than 10$^2$ (Table III). Sera from ovalbumin immunized calves did not bind to the surface of live *B. bigemina*.

TABLE III

Immunization of Cattle with Purified *B. bigemina* Merozoite Surface Proteins

| Antigen | Animal # | ELISA Titer | Surface IFA Titer | Peak % Parasitemia | Group Peak % Parasitemia$^a$ |
|---|---|---|---|---|---|
| Ovalbumin | B258 | — | — | 2.5 | 1.8 ± 0.7 |
| | B257 | — | — | 1.7 | |
| | B263 | — | — | 2.4 | |
| | B262 | — | — | 0.8 | |
| | B235 | — | — | 1.4 | |
| gp45 | B264 | 5 × 10$^4$ | 10$^2$ | 0.6 | 0.7 ± 0.1$^b$ |
| | B260 | 10$^4$ | 10$^2$ | 0.6 | |
| | B265 | 10$^4$ | 10$^2$ | 0.9 | |
| | B256 | 10$^4$ | 10$^2$ | 0.7 | |
| | B261 | 5 × 10$^4$ | 10$^2$ | 0.6 | |
| p58 | B279 | 10$^4$ | 10$^2$ | 0.3 | 0.8 ± 0.4$^b$ |
| | B277 | 10$^4$ | 10$^2$ | 0.9 | |
| | B274 | 10$^4$ | 10$^2$ | 1.2 | |
| | B273 | 5 × 10$^4$ | 10$^2$ | 0.9 | |
| | B272 | 5 × 10$^4$ | 10$^2$ | 0.5 | |
| gp55 | B271 | 10$^4$ | 10$^1$ | 0.6 | 0.8 ± 0.6$^b$ |
| | B275 | 10$^3$ | 10$^1$ | 0.6 | |
| | B276 | 10$^4$ | 10$^2$ | 0.5 | |
| | B278 | 10$^4$ | 10$^2$ | 0.6 | |
| | B238 | 10$^4$ | 10$^2$ | 1.9 | |
| gp36 | B266 | 10$^4$ | 10$^1$ | 1.8 | 1.4 ± 0.6 |
| | B267 | 10$^4$ | 10$^1$ | 1.7 | |
| | B268 | 10$^3$ | 10$^1$ | 2.0 | |
| | B269 | 10$^4$ | 10$^1$ | 0.4 | |
| | B270 | 10$^4$ | 10$^1$ | 1.2 | |

$^a$mean ± standard deviation
$^b$significantly different from ovalbumin controls, $p < 0.05$ 4. Challenge of immunized cattle with live *B. bigemina*

Each of the 25 calves immunized with a *B. bigemina* surface protein or ovalbumin was challenged by intravenous inoculation of fleshly harvested whole blood containing 3×10$^9$ parasites from a splenectomized donor calf. The results of this challenge are presented in Table III. No calves in the gp45 group and only 1 calf in the p58 and gp55 immunized groups had maximum parasitemias of 1% or greater after challenge, while 4/5 calves in the ovalbumin group and 4/5 calves in the gp36 group had peak parasitemias above 1%. This resulted in significant reduction (p<0.05) in mean peak parasitemia of the gp45, gp55, and p58 groups when compared to ovalbumin controls. The results clearly demonstrate that immunization with the novel purified merozoite surface proteins can significantly reduce risks associated with the disease.

5. Isolate cross-reactivity of merozoite surface proteins

To determine whether immunogenic epitopes of Mexico isolate merozoite surface proteins are conserved in other isolates, monospecific antisera from calves and rabbits immunized with purified antigens were reacted in immunoblots with gradient-separated merozoites from three additional Latin American isolates and one African isolate of *B. bigemina*. Antibodies bound to gp45 only in the homologous Mexico isolate and the Kenya isolate while antibodies in gp55 specific sera bound both Mexico isolates and the Kenya isolate. Molecular size heterogeneity between Latin American and Kenya isolates was present in both of these surface proteins. Antibodies in monospecific gp36 sera bound with a similar pattern to both Mexico isolates and the St. Croix isolate and bound weakly to 20 and 16 kDa polypeptides in the Kenya isolate. In contrast, antigenic and structural conservation was present in all isolates tested as evidenced by binding to all isolates tested. The molecular size of p58 was similar in all geographic isolates, although a closely spaced doublet was seen at 58,000 in the Kenya isolate.

L. Sequence Conservation Among Merozoite Apical Complex Proteins of Babesia bovis and *Babesia bigemina*

A neutralization sensitive *Babesia bigemina* merozoite surface protein, p58, and Bv60, a Babesia bovis merozoite surface protein, share an immunofluorescence pattern typical of apical complex polypeptides, and the Bv60 polypeptide has been localized to the secretory organelle, rhoptry, by immunoelectron microscopy. In contrast to other babesial merozoite surface proteins which are antigenically polymorphic among strains, surface exposed epitopes on p58 and Bv60 are conserved among all examined strains of *B. bigemina* and *B. bovis*, respectively. Based on these similarities, p58 and Bv60 may have similar functions in merozoite invasion of erythrocytes, the target cell for both *B. bigemina* and *B. bovis* in cattle.

Examination of p58 and Bv60 amino acid sequences was used to identify conserved regions that may direct common functions. Computer aided comparison between both nucleotide sequences using the software from the GCG package of the University of Wisconsin revealed 47% identity. The amino acid sequences have 35% identity and 57% similarity as determined using the BESTFIT program. Homology was greatest in the 300 amino acid block located at the amino terminus (45% identity and 65% similarity); these sequences are shown in FIG. 1. The 14 amino acid sequence PLSLPNPYQLDAAF (amino acids 114 through 127 in SEQ. ID 1) is strictly conserved in both polypeptides. In addition, there are several shorter oligopeptides within the amino terminal 300 residues that are identically conserved between p58 and Bv60 (FIG. 1). Between amino acids 76 to 101 in p58, and 80 to 105 in Bv60, there is a region containing four cysteine residues located in identical positions, suggesting that both polypeptides have a similar tertiary structure.

Published rhoptry and microneme protein sequences of other apicomplexan organisms were searched for similarity to the p58 and Bv60 polypeptide sequences (sequences of the *Theileria parva* 104 kD micronemerhoptry protein, *Plasmodium falciparum* rhoptry associated protein-1, *Plasmodium yoelii* rhoptry protein (3' region), and the *Plasmodium knowlesi* Duffy blood group receptor microneme polypeptide. The identical or a closely related 14 amino acid sequence was not present in the published sequences, indicating that the 14 amino acid oligopeptide does not mediate a common function in all rhoptry polypeptides. However, evaluation of overall sequence similarity among those apical complex polypeptides indicated significant sequence similarity among all published apicomplexan rhoptry and microneme sequences. The RDF program used for this determination compares a test sequence with randomly permuted versions of each potentially related sequence identified by the FASTP program. Highly significant scores (>3 standard deviations above the mean for permuted versions) were obtained among all the apical complex polypeptides tested. Table IV shows the evaluation of the statistical significance of sequence similarities among merozoite apical complex polypeptide using the program RDF. The RDF value indicated is the number of standard deviations above the mean optimized FASTP score of 20 shuffled sequences. p58: *B. bigemina* 58 kD apical complex protein; Bv60: *B. bovis* 60 kD apical complex protein; Tp: *Theileria parva* 104 kD micronemerhoptry protein; Pf: *Plasmodium falciparum* rhoptry associated protein-I; Py: *Plasmodium yoelii* rhoptry protein (3' region); Dr: Duffy receptor family of *Plasmodium knowlesi* (located in microhemes); Bv42: *B. bovis* merozoite outer membrane surface exposed protein.

TABLE IV

|      | Bv60 | p58 | Tp  | Pf   | Py   | Dr   | Bv42 |
|------|------|-----|-----|------|------|------|------|
| Bv60 | —    | 71  | 15  | 7.8  | 3.7  | 1.9  | −0.4 |
| p58  | 71   | —   | 13  | 8.4  | 4.3  | 6.5  | 1.6  |
| TP   | 15   | 13  | —   | 9.0  | 5.0  | 2.9  | 2.8  |
| Pf   | 7.8  | 8.4 | 9.0 | —    | 14.7 | 11.4 | 1.7  |
| Py   | 3.7  | 4.3 | 5.0 | 14.7 | —    | 11.5 | 0.1  |
| Dr   | 1.9  | 6.5 | 2.9 | 11.4 | 11.5 | —    | 1.4  |

In contrast, when apical complex proteins were compared to a *B. boris* merozoite surface protein (Bv42) unrelated to the apical complex, the RDF scores were <3 standard deviations above the means.

Conservation of the 14 residue oligopeptide in p58 and Bv60 from different *Babesia* species, despite changes in other regions of the polypeptide, suggest that this region mediates critical functions. Computer searches of data bases (EMBL release 26.0, Pir-Protein release 27.0, SwissProt release 17.0) did not identify any significant similarity of the 14 amino acid region to oligopeptides of known function such as enzymes or receptors. Thus, the conserved oligopeptide is possibly required for invasion of bovine erythrocytes. Invasion of different target cells by the related apicomplexan parasites may involve a similar mechanism mediated by different oligopeptides.

M. Enzyme Linked Immunosorbent Assay (ELISA)

Sera collected from experimental animals after immunizations 3, 4, and 5 were titered by ELISA against their respective immunogens. Microtiter plates were coated with 25, 50, and 100 ng/well of purified gp45, p58, gp55, and gp36 proteins, respectively, in 50 microliters of coating buffer (0.015M $Na_2CO_3$, 0.035 M $NaHCO_3$, pH 9.6). Plates were blocked with PBS containing 1% (w/v) bovine serum albumin (PBS-BSA) for 2 hours at 37° C., and rinsed 5 times with PBS containing 0.2% (v/v) Tween-20 (Sigma Chemical Co., St. Louis, Mo.) (PBS-Tween). Dilutions of serum in 50 microliters of PBS-BSA were added to each well, incubated for 1 hour, and the wells washed 5 times with PBS-Tween. Bound antibody was detected by addition of 50 microliters of peroxidase conjugated rabbit anti-bovine antibody diluted in PBS-BSA applied to each well for 1 hour, rinsing the wells as above, and adding 50 microliters of 5-aminosalicylate containing 0.005% (V/v) $H_2O_2$. The amount of color change was monitored by determining the $OD_{450/630}$ in an MR 600 Microplate Reader.

Diagnostic kits in accordance with this invention will typically utilize an antigenic protein which selectively binds to antibodies raised in animals exposed to *B. bigemina*. It is also possible to selectively detect antigens using monoclonal antibodies but such is not typically practical since better results will be obtainable when detecting the antibodies raised in the animals. Alternatively, it is possible to coat wells with merozoite antigen and detect antibodies in animals by their ability to inhibit binding of monoclonal antibody.

Diagnostic kits in accordance with the invention can be prepared as just described by coating a well or other surface with the antigen or antigens which specifically bind the antibody to be detected. Alternatively, it is possible to coat a well or other surface with monoclonal antibody or antibodies which bind prepared antigens, which in turn bind serum antibodies to be detected.

The bound serum antibodies can be detected by using an enzyme-linked antibody which binds the serum antibody, such as described above. Alternatively, it is possible to use radiolabeled secondary antibodies, fluorescent labeled secondary antibodies, or other labeling techniques which now exist or are hereafter developed for the same purposes.

N. Statistical Analysis

Means of the peak parasitemia for each group of calves immunized with a different protein were compared using one way analysis of variance and Duncan's method for multiple comparison of group means.

In compliance with the statute, the invention has been described in language more or less specific to as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

We claim:

1. A substantially pure *Babesia merozoite* surface protein obtainable from *Babesia bigemina*, said merozoite protein having a molecular weight of 45 kDa, wherein said merozoite protein, when inoculated into a bovid, is capable of inducing an immune response in said bovid which reduces the severity of babesiosis caused by *Babesia bigemina*.

2. A substantially pure *Babesia* merozoite surface protein obtainable from *Babesia bigemina*, said merozoite protein having a molecular weight of 55 kDa, wherein said merozoite protein, when inoculated into a bovid, is capable of inducing an immune response in said bovid which reduces the severity of babesiosis caused by *Babesia bigemina*.

3. A substantially pure *Babesia* merozoite surface protein obtainable from *Babesia bigemina*, said merozoite protein having a molecular weight of 58 kDa, wherein said merozoite protein, when inoculated into a bovid, is capable of inducing an immune response in said bovid which reduces the severity of babesiosis caused by *Babesia bigemina*.

4. The *Babesia* merozoite surface protein, according to claim 3, wherein
   said protein has the amino acid sequence shown in SEQ ID NO. 2.

* * * * *

UNITED STATES PATENT AND TRADEMARK OFFICE
CERTIFICATE OF CORRECTION

PATENT NO. : 5,422,428
DATED : June 6, 1995
INVENTOR(S) : Travis C. McGuire, et al It is certified that error appears in the above-indentified patent and that said Letters Patent is hereby corrected as shown below:

Column 1, line 21: Delete "jakirnovi" and insert --jakimovi--.

Column 1, line 22: Delete "antigenie" and insert --antigenic--.

Column 1, line 25: Delete "B. boris" and insert --B. bovis--.

Column 3, line 31: Delete "boris" and insert --bovis--.

Column 4, line 58: Delete "bigernina" and insert --bigemina--.

Column 7, line 18: Delete "35S-" and insert --$^{35}$S--.

Column 8, line 25: Delete "probe, Which" and insert --probe, which--.

Column 8, line 29: Delete "antigenie" and insert --antigenic--.

Column 8, line 35: Delete "bigeraina" and insert --bigemina--.

Column 8, line 63: Delete "w/th" and insert --with--.

Column 11, line 34: Delete "Percoil" and insert --Percoll--.

Column 11, line 45: Delete "the an using" and insert --the art using--.

Column 14, line 3: Delete "epffluorescence" and insert --epifluorescence--.

Column 14, line 46: Delete "Percoil" and insert --Percoll--.

Column 15, line 18: Delete "$^3$H-" and insert --$^3$H- --.

Column 15, line 44: Delete "J. lmmunol." and insert --J. Immunol.--.

UNITED STATES PATENT AND TRADEMARK OFFICE
CERTIFICATE OF CORRECTION

PATENT NO. : 5,422,428
DATED : June 6, 1995
INVENTOR(S) : Travis C. McGuire, et al It is certified that error appears in the above-indentified patent and that said Letters Patent is hereby corrected as shown below:

Column 15, line 56: Delete "antigert" and insert --antigen--.

Column 15, line 67: Delete "antigert" and insert --antigen--.

Column 16, line 46: Delete "Anal. Blochem." and insert --Anal. Biochem.--.

Column 18, line 12: Delete "multimerle proteins." and insert --multmeric proteins.--

Column 18, line 21: Delete "antigenie" and insert --antigenic--.

Column 18, line 32: Delete "eDNA" and insert --cDNA--.

Column 18, line 33: Delete "eDNA" and insert --cDNA--.

Column 19, line 2: Delete "$^{125}$1 - Protein" and insert --$^{125}$I - Protein--.

Column 21, line 10: Delete "Blochem." and insert --Biochem.--.

Column 21, line 13: Delete "eDNA" and insert --cDNA--.

Column 21, lines 21-22: Delete "20 All 1XPCR" and insert --20 $\mu$l 1XPCR--.

Column 21, lines 50-68 through Column 22, lines 1-24: 6. In vitro translation studies....processed as above for immunoscreening.

Pages transposed in patent. Move these lines to Column 22, after line 68 for proper sequence.

UNITED STATES PATENT AND TRADEMARK OFFICE
CERTIFICATE OF CORRECTION

PATENT NO. : 5,422,428
DATED : June 6, 1995
INVENTOR(S) : Travis C. McGuire, et al It is certified that error appears in the above-indentified patent and that said Letters Patent is hereby corrected as shown below:

Column 25, line 66: Delete "antigert" and insert --antigen--.

Column 26, line 22: Delete "104" and insert --$10^4$--.

Column 26, line 64: Delete "fleshly" and insert --freshly--.

Column 27, line 26: Delete "antigenie" and insert --antigenic--.

Column 28, line 1: Delete "positions, . suggesting" and insert --positions, suggesting--.

Column 28, line 33: Delete "protein - I;" and insert --protein - 1;--.

Column 28, lines 35-36: Delete "microhemes)" and insert --micronemes)--.

Column 28, line 43: Delete "TP" and insert --Tp--.

Column 28, line 49: Delete "B. boris" and insert --B. Bovis--.

Column 29, line 16: Delete "(V/v)" and insert --(v/v)--.

Column 35, Claim 1: Delete "A substantially pure *Babesia* merozite surface protein obtainable from *Babesia bigemina*, said merozoite protein having a molecular weight of 45 kDa, wherein said merozite protein, when inoculated into a bovid, is capable of inducing an immune response in said bovid which reduces the severity of babesiosis caused by *Babesia bigemina*." and insert --An isolated and purified *Babesia bigemina* merozoite surface protein, gp45, having a molecular mass of 45 kDa as determined by SDS-PAGE, capable of binding monoclonal antibody 14.1 (ATCC accession number HB 9377), and being capable of inducing an immune response in a bovid which reduces the severity of babesiosis caused by *Babesia bigemina*.--

UNITED STATES PATENT AND TRADEMARK OFFICE
CERTIFICATE OF CORRECTION

PATENT NO. : 5,422,428
DATED : June 6, 1995
INVENTOR(S) : Travis C. McGuire, et al It is certified that error appears in the above-indentified patent and that said Letters Patent is hereby corrected as shown below:

Column 37, line 5, Claim 2: Delete "A substantially pure *Babesia* merozoite surface protein obtainable from *Babesia bigemina*, said merozoite protein having a molecular weight of 55 kDa, wherein said merozoite protein, when inoculated into a bovid, is capable of inducing an immune response in said bovid which reduces the severity of babesiosis caused by *Babesia bigemina*." and insert --An isolated and purified *Babesia bigemina* merozoite surface protein, gp55, having a molecular mass of 55 kDa as determined by SDS-PAGE, capable of binding monoclonal antibody 14.20 (ATCC accession number HB 9376), and being capable of inducing an immune response in a boid which reduces the severity of babesiosis caused by *Babesia bigemina*.--

Column 38, line 1, Claim 3: Delete "A substantially pure *Babesia* merozoite surface protein obtainable from *Babesia bigemina*, said merozoite protein having a molecular weight of 58 kDa, wherein said merozoite protein, when inoculated into a bovid, is capable of inducing an immune response in said bovid which reduces the severity of babesiosis caused by *Babesia bigemina*" and insert -- An isolated and purified *Babesia bigemina* merozoite surface protein having a molecular mass of 58 kDa as determined by SDS-PAGE, capable of binding monoclonal antibody 14.16 (ATCC accession number HB 9379), and being capable of inducing an immune response in a bovid which reduces the severity of babesiosis caused by *Babesia bigemina*.--

UNITED STATES PATENT AND TRADEMARK OFFICE
CERTIFICATE OF CORRECTION

PATENT NO. : 5,422,428
DATED : June 6, 1995
INVENTOR(S) : Travis C. McGuire, et al It is certified that error appears in the above-indentified patent and that said Letters Patent is hereby corrected as shown below:

Column 38, line 8, Claim 4: Delete "The *Babesia* merozoite surface protein, according to claim 3, wherein said protein has the amino acid sequence shown in SEQ ID NO. 2." and insert --The protein, according to claim 3, having the amino acid sequence as shown in SEQ ID NO. 2.--

Signed and Sealed this

Nineteenth Day of September, 1995

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO.    : 5,422,428
DATED         : June 6, 1995
INVENTOR(S)   : Travis C. McGuire, Terry F. McElain, Lance E. Perryman, William C. Davis It is certified that error appears in the above-identified patent and that said Letters Patent is hereby corrected as shown below:

Column 1,
Line 5, insert the following:
-- The subject invention was made with government support under USAID Grant Nos. DAN-4178-A-00-7056-00, DHR-5600-G-00-1035-00, and HRN-5600-F-00-2034-00; USDA Grant Nos. NRICGP-92-37204-8180, 88-34135-3508, and 86-CRSR-2-2842; and USDA-BARD Grant Nos. US-1855-90RC and US-1080-86. The government has certain rights in this invention. --

Signed and Sealed this

Eleventh Day of September, 2001

*Attest:*

*Attesting Officer*

NICHOLAS P. GODICI
*Acting Director of the United States Patent and Trademark Office*